US012688581B2

(12) United States Patent
Yoo et al.

(10) Patent No.: US 12,688,581 B2
(45) Date of Patent: ***Jul. 21, 2026

(54) METHOD AND APPARATUS FOR PROVIDING INFORMATION ASSOCIATED WITH IMMUNE PHENOTYPES FOR PATHOLOGY SLIDE IMAGE

(71) Applicant: LUNIT INC., Seoul (KR)

(72) Inventors: Donggeun Yoo, Seoul (KR); Chanyoung Ock, Seoul (KR); Kyunghyun Paeng, Seoul (KR)

(73) Assignee: LUNIT INC., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/463,912

(22) Filed: Sep. 8, 2023

(65) Prior Publication Data

US 2023/0419492 A1     Dec. 28, 2023

Related U.S. Application Data

(63) Continuation of application No. 17/502,661, filed on Oct. 15, 2021, which is a continuation of application No. PCT/KR2021/005772, filed on May 7, 2021.

(30) Foreign Application Priority Data

| | | |
|---|---|---|
| May 8, 2020 | (KR) | 10-2020-0055483 |
| Apr. 27, 2021 | (KR) | 10-2021-0054206 |
| May 7, 2021 | (KR) | 10-2021-0059519 |

(51) Int. Cl.
*G06T 7/00* (2017.01)
*G06N 3/02* (2006.01)
*G16B 20/00* (2019.01)

(52) U.S. Cl.
CPC ............. *G06T 7/0012* (2013.01); *G06N 3/02* (2013.01); *G16B 20/00* (2019.02)

(58) Field of Classification Search
None
See application file for complete search history.

(56) References Cited

U.S. PATENT DOCUMENTS

| | | | |
|---|---|---|---|
| 10,585,032 B2 | 3/2020 | Fukuda et al. | |
| 11,436,718 B2 | 9/2022 | Yoshida et al. | |
| 2014/0377221 A1 | 12/2014 | Tufaro et al. | |
| 2017/0169567 A1 | 6/2017 | Chefd'hotel et al. | |
| 2017/0285029 A1 | 10/2017 | Hanks et al. | |
| 2017/0352157 A1 | 12/2017 | Madabhushi et al. | |
| 2018/0357816 A1 | 12/2018 | Gholap et al. | |
| 2019/0287240 A1 | 9/2019 | Gaire et al. | |
| 2021/0103757 A1 | 4/2021 | Jang | |
| 2023/0177682 A1* | 6/2023 | Xiao | G06T 7/11 |
| | | | 382/133 |

FOREIGN PATENT DOCUMENTS

| | | |
|---|---|---|
| EP | 3 108 446 B1 | 3/2019 |
| JP | 2017-509871 A | 4/2017 |
| JP | 2017-516992 A | 6/2017 |
| JP | 2018-100976 A | 6/2018 |
| JP | 2019-95212 A | 6/2019 |
| KR | 10-2003-0066766 | 8/2003 |
| KR | 10-2015-0008846 A | 1/2015 |
| KR | 10-1889723 | 8/2018 |
| KR | 10-2068279 B1 | 1/2020 |
| WO | 2015/069827 A2 | 5/2015 |
| WO | 2019/108888 A1 | 6/2019 |
| WO | 2019/110583 A1 | 6/2019 |
| WO | 2020/083970 A1 | 4/2020 |
| WO | 2022/047412 A1 | 3/2022 |

OTHER PUBLICATIONS

Kather et al. (eLife (2018) vol. 7:19 pages).*
Echarti et al. (Cancer (2019) vol. 11:13 pages).*
Lanitis et al. (Annals of Oncology (2017) vol. 28 (Supplement 12):15 pages).*
Parra et al., "Validation of multiplex immunofluorescence panels using multispectral microscopy for immune-profiling of formalin-fixed and paraffin-embedded human tumor tissues", Scientific Reports, Oct. 17, 2017, vol. 7/No. 13380, pp. 1-11 (11 total pages).
International Search Report for PCT/KR2021/005772, dated Aug. 13, 2021.
Daniel S. Chen, et al., "Elements of cancer immunity and the cancer—immune set point", Nature, Jan. 19, 2017, vol. 541, pp. 321-330 (10 pages).
Extended European Search Report dated Jun. 11, 2024 in Application No. 21800694.8.
Communication issued Jan. 28, 2025 in Japanese Patent Application No. 2022-561179.
Communication issued Feb. 18, 2025 in Japanese Patent Application No. 2022-556072.
Pramod Darvin et al., "Immune checkpoint inhibitors: recent progress and potential biomarkers", Experimental & Molecular Medicine, 2018, vol. 50, No. 165 (11 pages).
Office Action issued in the U.S. Appl. No. 17/502,661 mailed May 19, 2026.
"Xing et al., Robust Nucleas/Cell Detection and Segmentation in Digital Pathology and Microscopy Images: A comprehensive Review, 2016, IEE Reviews in Biomedical Engineering, 9, p. 234-263 (Year:2016)".
"Tomita et al., Attention-based deep neural networks for Detection of Cancerous and Precancerous Esophagus Tissue on Histopathological slides, 2019, JAMM Network Open, 2(11), p. 1-13 and Suppl. (Year: 2019)".

* cited by examiner

*Primary Examiner* — Lori A. Clow
(74) *Attorney, Agent, or Firm* — Sughrue Mion, PLLC

(57) ABSTRACT

The present disclosure relates to a method, performed by at least one computing device, for providing information associated with immune phenotype for a pathology slide image. The method may include obtaining information associated with immune phenotype for one or more regions of interest (ROIs) in a pathology slide image, generating, based on the information associated with the immune phenotype for one or more ROIs, an image indicative of the information associated with the immune phenotype, and outputting the image indicative of the information associated with immune phenotype.

20 Claims, 12 Drawing Sheets

FIG. 2

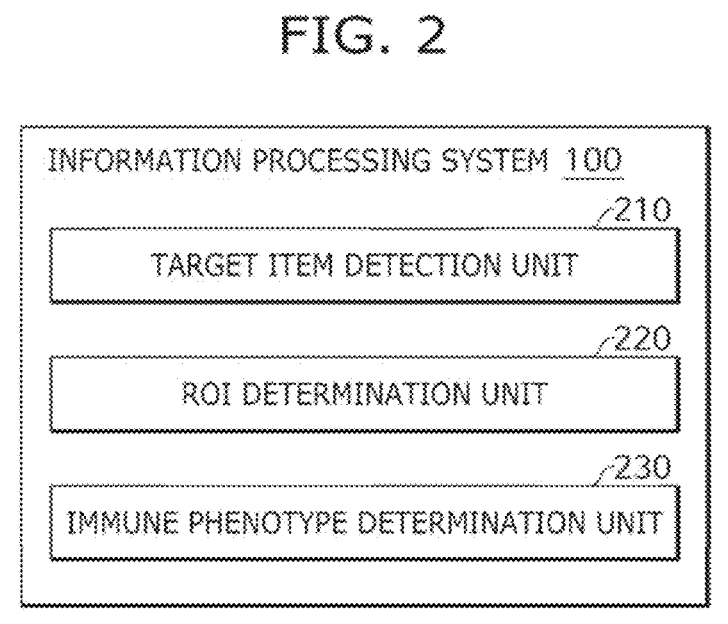

INFORMATION PROCESSING SYSTEM  100

/210

TARGET ITEM DETECTION UNIT

/220

ROI DETERMINATION UNIT

/230

IMMUNE PHENOTYPE DETERMINATION UNIT

IMMUNE PHENOTYPE DETERMINATION RESULT

230

IMMUNE PHENOTYPE DETERMINATION UNIT

1ST ROI 612

2ND ROI 614

3RD ROI 616

METHOD AND APPARATUS FOR PROVIDING INFORMATION ASSOCIATED WITH IMMUNE PHENOTYPES FOR PATHOLOGY SLIDE IMAGE

CROSS-REFERENCE TO RELATED APPLICATIONS

This application is a continuation of U.S. application Ser. No. 17/502,661 filed Oct. 15, 2021, which is a continuation of International Application No. PCT/KR2021/005772 filed on May 7, 2021 which claims priority to Korean Patent Application No. 10-2020-0055483 filed on May 8, 2020, Korean Patent Application No. 10-2021-0054206 filed on Apr. 27, 2021, and Korean Patent Application No. 10-2021-0059519 filed on May 7, 2021, the entire contents of which are herein incorporated by reference.

TECHNICAL FIELD

The present disclosure relates to a method and a device for providing information associated with immune phenotype for pathology slide image, and more specifically, to a method and a device for generating and outputting an image indicative of information associated with immune phenotype for one or more regions of interest (ROIs) in a pathology slide image.

BACKGROUND ART

Recently, a third-generation anticancer drug for cancer treatment, that is, the immune checkpoint inhibitor that utilize the immune system of the patient's body has gained attention. By the immune anticancer drug, it may refer to any drug that prevents cancer cells from evading the body's immune system or makes immune cells better recognize and attack cancer cells. Since it acts through the body's immune system, there are few side effects from the anticancer drugs, and the survival period of cancer patients treated with the immune checkpoint inhibitor may be longer than when treated with other anticancer drugs. However, these immune checkpoint inhibitor are not always effective for all cancer patients. Therefore, it is important to predict the response rate of the immune checkpoint inhibitor in order to predict the effect of the immune checkpoint inhibitor on the current cancer patient.

Meanwhile, in order to predict the response to the immune checkpoint inhibitor, a user (e.g., a doctor, a patient, and the like) may be provided with immune response information generated through a pathology slide image of a patient's tissue. According to the related art, the user (e.g., doctor, patient, and the like) may be provided with information on the immune response (e.g., immune cell expression information, and the like) to each of the plurality of patches included in the pathology slide image in order to predict the reactivity of the immune checkpoint inhibitor. In this case, it may be difficult for the user to intuitively recognize immune response information for each of numerous patches included in the pathology slide image. In addition, the immune response information may also be generated for a patch among a plurality of patches that is substantially unnecessary for predicting the response to the immune checkpoint inhibitor.

SUMMARY

Technical Problem

The present disclosure provides a method and a device for providing information associated with immune phenotype for pathology slide image to solve the problems described above.

Technical Solution

The present disclosure may be implemented in various ways, including a method, a device (system), a computer readable storage medium storing instructions, or a computer program.

According to an embodiment of the present disclosure, a method, performed by at, least one computing device, for providing information associated with immune phenotype for pathology slide image includes obtaining information associated with immune phenotype for one or more regions of interest (ROIs) in a pathology slide image, generating, based on the information associated with the immune phenotype for one or more ROIs, an image indicative of the information associated with the immune phenotype, and outputting the image indicative of the information associated with immune phenotype.

According to an embodiment, the one or more ROIs are determined based on a detection result for one or more target items for the pathology slide image.

According to an embodiment, the one or more ROIs include at least some regions in the pathology slide image that, satisfy a condition associated with the one or more target items.

According to an embodiment, the one or more ROIs are regions being output upon input of the detection result for the one or more target items for the pathology slide image or the pathology slide image to an ROI extraction model, and the ROI extraction model is trained to output a reference ROI upon input of the detection result for one or more target items for a reference pathology slide image or a reference pathology slide image.

According to an embodiment, the obtaining includes obtaining the immune phenotype of the one or more ROIs, the generating includes generating an image including a visual representation corresponding to the immune phenotype of the one or more ROIs, and the immune phenotype includes at least one of immune inflamed, immune excluded, or immune desert.

According to an embodiment, the obtaining includes obtaining one or more immune phenotype scores for the one or more ROIs, the generating includes generating an image including a visual representation corresponding to the one or more immune phenotype scores, and the one or more immune phenotype scores include at least one of a score for immune inflamed, a score for immune excluded, or a score for immune desert.

According to an embodiment, the obtaining includes obtaining a feature associated with one or more immune phenotypes for the one or more ROIs, the generating includes generating an image including a visual representation corresponding to the feature associated with the one or more immune phenotypes, and the feature associated with the one or more immune phenotypes includes at least one of a statistical value or a vector associated with the immune phenotype.

According to an embodiment, the outputting includes outputting one or more ROIs in the pathology slide image together with an image including a visual representation.

According to an embodiment, the outputting may include overlaying the image including the visual representation on one or more ROIs in the pathology slide image.

According to an embodiment, the method further includes obtaining a detection result for one or more target items from the pathology slide image, generating an image indicative of the detection result for one or more target items, and outputting the image indicative of the detection result for one or more target items.

There may be provided a computer program stored in a computer-readable recording medium for executing, on a computer, the method for providing the information associated with the immune phenotype for the pathology slide image described above according to an embodiment of the present disclosure.

A computing device according to an embodiment may include a memory storing one or more instructions, and a processor configured to execute the stored one or more instructions to obtain information associated with immune phenotype for one or more ROIs in the pathology slide image, generate, based on the information associated with the immune phenotype for one or more ROIs, an image indicative of the information associated with the immune phenotype, and output the image indicative of the information associated with the immune phenotype.

Advantageous Effects

According to some embodiments of the present disclosure, by providing the user with an image visually representing the information associated with immune phenotype, it is possible to enable the user to intuitively recognize the information associated with immune phenotype for each region. In addition, by providing a visual representation indicative of the information associated with immune phenotype by overlaying it on a corresponding ROI in a pathology slide image, it is possible to enable the user to recognize at a glance which region of the pathology slide image corresponds to the information indicated by the corresponding visual representation.

According to some embodiments of the present, disclosure, in order to determine the immune phenotype and/or response or non-response to the immune checkpoint inhibitor, the ROI in the pathology slide image which actually requires analysis may be determined. That is, instead of analyzing the entire pathology slide image, the information processing system and/or the user terminal may perform processing (e.g., determining an immune phenotype and/or calculating an immune phenotype score, and the like) only on the ROIs while excluding the regions where analysis is unnecessary, such that computer resources, processing costs, and the like can be minimized.

According to some embodiments of the present disclosure, more accurate results can be provided by processing (e.g., determining an immune phenotype and/or calculating an immune phenotype score, and the like) only on the significant region when determining the immune phenotype and/or determining response or non-response to the immune checkpoint inhibitor.

The effects of the present disclosure are not limited to the effects described above, and other effects not described will be able to be clearly understood by those of ordinary skill in the art (hereinafter, referred to as "ordinary technician") from the description of the claims.

BRIEF DESCRIPTION OF THE DRAWING

Embodiments of the present disclosure will be described with reference to the accompanying drawings described below, in which like reference numerals denote like elements, but are not limited thereto.

FIG. 2 is a block diagram illustrating an internal configuration of the information processing system according to an embodiment of the present disclosure.

FIG. 6 is a diagram illustrating an example of generating an immune phenotype determination result according to an embodiment of the present disclosure.

DETAILED DESCRIPTION

Figure 1:
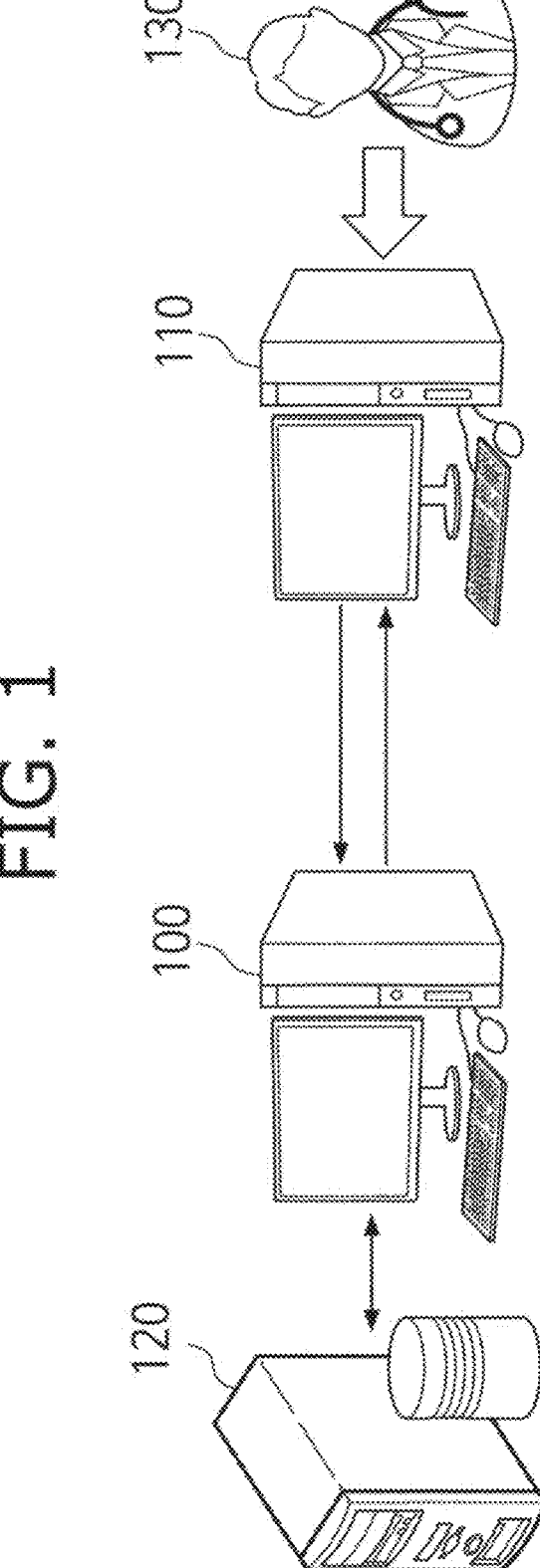
FIG. 1 is an exemplary configuration diagram illustrating a system in which an information processing system provides information associated with immune phenotype for pathology slide image according to an embodiment of the present disclosure.

Hereinafter, specific details for the practice of the present disclosure will be described in detail with reference to the accompanying drawings. However, in the following description, detailed descriptions of well-known functions or configurations will be omitted when it may make the subject matter of the present disclosure rather unclear.

In the accompanying drawings, the same or corresponding elements are assigned the same reference numerals. In addition, in the following description of the embodiments, duplicate descriptions of the same or corresponding components may be omitted. However, even if descriptions of elements are omitted, it is not intended that such elements are not included in any embodiment.

Advantages and features of the disclosed embodiments and methods of accomplishing the same will be apparent by referring to embodiments described below in connection with the accompanying drawings. However, the present disclosure is not limited to the embodiments disclosed below, and may be implemented in various different forms, and the present embodiments are merely provided to make the present disclosure complete, and to fully disclose the scope of the invention to those skilled in the art to which the present disclosure pertains.

The terms used herein will be briefly described prior to describing the disclosed embodiments in detail. The terms used herein have been selected as general terms which are widely used at present in consideration of the functions of the present disclosure, and this may be altered according to the intent of an operator skilled in the art, conventional practice, or introduction of new technology. In addition, in a specific case, a term is arbitrarily selected by the applicant, and the meaning of the term will be described in detail in a corresponding description of the embodiments. Therefore, the terms used in the present, disclosure should be defined based on the meaning of the terms and the overall contents of the present disclosure rather than a simple name of each of the terms.

As used herein, the singular forms "a," "an," and "the" are intended to include the plural forms as well, unless the context clearly indicates the singular forms. Further, the plural forms are intended to include the singular forms as well, unless the context clearly indicates the plural forms. As used throughout the description, when one part is referred to as "comprising" (or "including" or "having") other elements, the part can comprise (or include or have) only those elements or other elements as well as those elements unless specifically described otherwise.

Further, the term "module" or "unit" used herein refers to a software or hardware component, and "module" or "unit" performs certain roles. However, the meaning of the "module" or "unit" is not limited to software or hardware. The "module" or "unit" may be configured to be in an addressable storage medium or configured to reproduce one or more processors. Accordingly, as an example, the "module" or "unit" may include components such as software components, object-oriented software components, class components, and task components, and at least one of processes, functions, attributes, procedures, subroutines, program code segments of program code, drivers, firmware, micro-codes, circuits, data, database, data structures, tables, arrays, and variables. Furthermore, functions provided in the components and the "modules" or "units" may be combined into a smaller number of components and "modules" or "units", or further divided into additional components and "modules" or "units."

According to an embodiment, the "module" or "unit" may be implemented as a processor and a memory. The "processor" should be interpreted broadly to encompass a general-purpose processor, a central processing unit (CPU), a microprocessor, a digital signal processor (DSP), a controller, a microcontroller, a state machine, and so forth. Under some circumstances, the "processor" may refer to an application-specific integrated circuit (ASIC), a programmable logic device (PLD), a field-programmable gate array (FPGA), and so on. The "processor" may refer to a combination of processing devices, e.g., a combination of a DSP and a microprocessor, a plurality of microprocessors, one or more microprocessors in conjunction with a DSP core, or any other combination of such configurations. In addition, "memory" should be interpreted broadly to encompass any electronic component capable of storing electronic information. The "memory" may refer to various types of processor-readable media such as random access memory (RAM), read-only memory (ROM), non-volatile random access memory (NVRAM), programmable read-only memory (PROM), erasable programmable read-only memory (EPROM), electrically erasable PROM (EEPROM), flash memory, magnetic or optical data storage, registers, and so on. The memory is said to be in electronic communication with a processor if the processor can read information from and/or write information to the memory. The memory integrated with a processor is in electronic communication with the processor.

In the present disclosure, the "system" may refer to at least one of a server device and a cloud device, but not limited thereto. For example, the system may include one or more server devices. As another example, the system may include one or more cloud devices. As another example, the system may be configured together with both a server device and a cloud device and operated.

In the present disclosure. "target data" may refer to any data or data item that can be used for training of a machine learning model, and may include, for example, data indicative of an image, data indicative of voice or voice characteristics, and the like, but is not limited thereto. In the present disclosure, the whole pathology slide image and/or at least one patch (or region) included in the pathology slide image are explained as the target data, but is not limited thereto, and any data that can be used for training a machine learning model may correspond to the target data. In addition, the target data may be tagged with label information through an annotation task.

In the present disclosure, the "pathology slide image" refers to an image obtained by capturing a pathological slide fixed and stained through a series of chemical treatments in order to observe a tissue removed from a human body with a microscope. For example, the pathology slide image may refer to a digital image captured with a microscope, and may include information on cells, tissues, and/or structures in the human body, in addition, the pathology slide image may include one or more patches, and the one or more patches may be tagged with label information (e.g., information on immune phenotype) through the annotation work. For example, the "pathology slide image" may include H&E-stained tissue slides and/or IHC-stained tissue slides, but is not limited thereto, and tissue slides applied with various staining methods (e.g., chromogenic in situ hybridization (CISH), Fluorescent in situ hybridization (FISH). Multiplex IHC, and the like), or unstained tissue slides may also be included. As another example, the "pathology slide image" may be a patient's tissue slide generated to predict a response to immune checkpoint inhibitor, and it may include a tissue slide of a patient before treatment with immune checkpoint inhibitor and/or a tissue slide of a patient after treatment with immune checkpoint inhibitor.

In the present disclosure, a "biomarker" may be defined as a marker that can objectively measure a normal or pathology state, a degree of response to a drug, and the like. For example, the biomarker may include immune checkpoint inhibitor and PD-L1 as a biomarker, but is not limited thereto, and may include Tumor Mutation Burden (TMB) value. Microsatellite Instability (MSI) value, Homologous Recombination Deficiency (HRD) value, CD3, CD8, CD68, FOXP3, CD20, CD4, CD45, CD63, and other various biomarkers related to immune cells.

In the present disclosure, the "patch" may refer to a small region within the pathology slide image. For example, the patch may include a region corresponding to a semantic object extracted by performing segmentation on the pathology slide image. As another example, the patch may refer to a combination of pixels associated with the label information generated by analyzing the pathology slide image.

In the present disclosure, the "regions of interest (ROIs)" may refer to at least some regions to be analyzed in the pathology slide image. For example, the ROIs may refer to at least some regions in the pathology slide image that include a target item. As another example, the ROIs may refer to at least some of a plurality of patches generated by segmenting the pathology slide image.

In the present disclosure, a "machine learning model" and/or an "artificial neural network model" may include any model that is used for inferring an answer to a given input. According to an embodiment, the machine learning model may include an artificial neural network model including an input layer (layer), a plurality of hidden layers, and output layers. In an example, each layer may include a plurality of nodes. For example, the machine learning model may be trained to infer label information for pathology slide images and/or at least one patch included in the pathology slides. In this case, the label information generated through the annotation task may be used to train the machine learning model. In addition, the machine learning model may include weights associated with a plurality of nodes included in the machine learning model. In an example, the weight may include an any parameter associated with the machine learning model.

In the present disclosure, "training" may refer to any process of changing a weight associated with the machine learning model using at least one patch and the label information. According to an embodiment, the training may refer to a process of changing or updating weights associated with the machine teaming model through one or more of forward propagation and backward propagation of the machine learning model using at least one patch and the label information.

In the present disclosure, the "label information" is correct answer information of the data sample information, which is obtained as a result of the annotation task. The label or label information may be used interchangeably with terms such as annotation, tag, and so on as used in the art. In the present disclosure, the "annotation" may refer to an annotation work and/or annotation information (e.g., label information, and the like) determined by performing the annotation work. In the present disclosure, the "annotation information" may refer to information for the annotation work and/or information generated by the annotation work (e.g., label information).

In the present disclosure, the "target item" may refer to data/information, an image region, an object, and the like to be detected in the pathology slide image. According to an embodiment, the target item may include a target to be detected from the pathology slide image for diagnosis, treatment, prevention, or the like of a disease (e.g., cancer). For example, the "target item" may include a target item in units of cells and a target item in units of areas.

In the present disclosure. "each of a plurality of A" and/or "respective ones of a plurality of A" may refer to each of all components included in the plurality of A, or may refer to each of some of the components included in a plurality of A. For example, each of the plurality of ROIs may refer to each of all ROIs included in the plurality of ROIs or may refer to each of some ROIs included in the plurality of ROIs.

In the present disclosure, "instructions" may refer to one or more instructions grouped based on functions, which are the components of a computer program and executed by the processor.

In the present disclosure, a "user" may refer to a person who uses a user terminal. For example, the user may include an annotator who performs an annotation work. As another example, the user may include a doctor, a patient, and the like who is provided with the information associated with immune phenotype and/or a prediction result of a response to immune checkpoint inhibitor (e.g., a prediction result as to whether or not the patient responds to immune checkpoint inhibitor). In addition, the user may refer to the user terminal, or conversely, the user terminal may refer to the user. That is, the user and the user terminal may be interchangeably used herein.

FIG. 1 is an exemplary configuration diagram illustrating a system in which an information processing system 100 provides information associated with immune phenotype for pathology slide image according to an embodiment of the present disclosure. As illustrated, the system for providing information associated with immune phenotype for pathology slide image may include the information processing system 100, a user terminal 110, and a storage system 120. In an example, the information processing system 100 may be configured to be connected to each of the user terminal 110 and the storage system 120 for communication. While FIG. 1 illustrates one user terminal 110, the present disclosure is not limited thereto, and in an exemplary configuration, a plurality of user terminals 110 may be connected to the information processing system 100 for communication. In addition, while the information processing system 100 is shown as one computing device in FIG. 1, embodiment is not limited thereto, and the information processing system 100 may be configured to process information and/or data in a distributed manner through a plurality of computing devices. In addition, while the storage system 120 is shown as a single device in FIG. 1, embodiment is not limited thereto, and the system may be configured with a plurality of storage devices or as a system that supports a cloud. In addition, the respective components of the system for providing information associated with immune phenotype of a pathology slide image illustrated in FIG. 1 represent functional components divided on the basis of functions, and in an actual physical environment, a plurality of components may be implemented as being incorporated with each other.

The information processing system 100 and the user terminal 110 are any computing devices used to generate and provide the information associated with immune phenotype for pathology slide image. In an example, the computing device may refer to any type of device equipped with a computing function, and may be a notebook, a desktop, a laptop, a server, a cloud system, and the like, for example, but is not limited thereto.

The information processing system 100 may receive a pathology slide image. For example, the information processing system 100 may receive the pathology slide image from the storage system 120 and/or the user terminal 110. The information processing system 100 may generate information associated with immune phenotype of the pathology slide image and provide it to the user 130 through the user terminal 110, in an embodiment, the information processing system 100 may determine one or more ROIs in the pathology slide image and generate information associated with immune phenotype for the one or more ROIs. In this example, the information associated with immune phenotype may include at least one of an immune phenotype of one or more ROIs, an immune phenotype score of one or more ROIs, and a feature associated with the immune phenotype of one or more ROIs.

In an embodiment, the information processing system 100 may determine one or more ROIs based on a detection result for one or more target items for the pathology slide image. For example, the information processing system 100 may determine one or more ROIs including at least some regions in the pathology slide image that satisfy a condition associated with the one or more target items. Additionally or alternatively, upon input of the detection result for one or more target items for a pathology slide image (e.g., a pathology slide image including a detection result for target item) to a region-of-interest (ROI) extraction model, the information processing system 100 may determine regions being output as one or more ROIs. In this example, the ROI extraction model may correspond to a model trained to output a reference ROI when the detection result for one or more target items for reference pathology slide image (e.g., a reference pathology slide image including the detection result for target item) is input.

The user terminal 110 may obtain from the information processing system 100 the information associated with immune phenotype for one or more ROIs in the pathology slide image. For example, the information associated with immune phenotype for one or more ROIs may include an immune phenotype (e.g., at least one of immune inflamed, immune excluded, or immune desert) for one or more ROIs. Additionally or alternatively, the information associated with immune phenotype for one or more ROIs may include one or more immune phenotype scores for the one or more ROIs (e.g., the immune phenotype score is at least one of a score for immune inflamed, a score for immune excluded or a score for immune desert). Additionally or alternatively, the information associated with immune phenotype for one or more ROIs may include a feature associated with one or more immune phenotypes for one or more ROIs (e.g., at least one of statistical value or vector associated with the immune phenotype).

Then, the user terminal 110 may generate an image indicative of the information associated with immune phenotype based on the information associated with immune phenotype for one or more ROIs. In an embodiment, the user terminal 110 may generate an image including a visual representation corresponding to the immune phenotype of one or more ROIs. In another embodiment, the user terminal 110 may generate an image including a visual representation corresponding to the one or more immune phenotype scores. For example, the visual representation may include color (e.g., color, brightness, saturation, and the like), text, image, mark, figure, and the like.

The user terminal 110 may output an image indicative of the information associated with the generated immune phenotype. In an embodiment, the user terminal 110 may output one or more ROIs in the pathology slide image together with an image including a visual representation. That is, the one or more ROIs in the pathology slide image and the image including the visual representation may be displayed together on the display device associated with the user terminal 110. In another embodiment, the user terminal 110 may overlay the image including the visual representation on one or more ROIs in the pathology slide image. That is, one or more ROIs in the pathology slide image overlaid with the image including the visual representation may be displayed on the display device associated with the user terminal 110. Accordingly, the user 130 (e.g., doctor, patient, and the like) may be provided with an image indicative of information associated with immune phenotype through the user terminal 110.

The storage system 120 is a device or a cloud system that stores and manages pathology slide images associated with a target patient and various data associated with a machine learning model to provide information associated with immune phenotype for the pathology slide image. For efficient data management, the storage system 120 may store and manage various types of data using a database. In this example, the various data may include any data associated with the machine learning model, and include, for example, a file of the target data, meta information of the target data, label information for the target data that is the result of the annotation work, data related to the annotation work, a machine learning model (e.g., an artificial neural network model), and the like, but are not limited thereto. While FIG. 1 shows the information processing system 100 and the storage system 120 as separate systems, embodiment is not limited thereto, and they may be incorporated into one system.

According to some embodiments of the present disclosure, by providing the user 130 with an image visually representing the information associated with immune phenotype, it is possible to enable the user 130 to intuitively recognize the information associated with immune phenotype for each region. In addition, according to some embodiments of the present disclosure, in order to determine the immune phenotype and/or response or non-response to the immune checkpoint inhibitor, the ROI in the pathology slide image which actually requires analysis may be determined. That is, instead of analyzing the entire pathology slide image, the information processing system 100 and/or the user terminal 110 may perform processing (e.g., determining an immune phenotype and/or calculating an immune phenotype score, and the like) only on the ROIs while excluding the regions where analysis is unnecessary, such that computer resources, processing costs, and the like can be minimized. In addition, more accurate prediction results may be provided by processing (e.g., determining an immune phenotype and/or calculating art immune phenotype score, and the like) only on the significant region when determining the immune phenotype and/or determining response or non-response to the immune checkpoint inhibitor.

FIG. 2 is a block diagram illustrating an internal configuration of the information processing system 100 according to an embodiment of the present disclosure. In order to provide the information associated with immune phenotype for the pathology slide image, the information processing system 100 may generate the information associated with immune phenotype for the pathology slide image. According to an embodiment, as illustrated, the information processing system 100 may include a target item detection unit 210, an ROI determination unit 220, and an immune phenotype determination unit 230. Respective components of the information processing system 100 illustrated in FIG. 2 represent functional components that can be divided on the basis of functions, and in an actual physical environment, a plurality of components may be implemented as being incorporated with each other.

The target item detection unit 210 may receive the pathology slide image (e.g., H&E-stained pathology slide image, IHC-stained pathology slide image, and the like), and detect one or more target items in the received pathology slide image. In an embodiment, the target item detection unit 210 may use the artificial neural network model for target item detection to detect one or more target items in the pathology slide image. In this example, the artificial neural network model for target item detection may correspond to a model trained to detect one or more reference target items from the reference pathology slide image. For example, the target item detection unit 210 may detect a target item in units of cells and/or a target item in units of regions in the pathology slide image. That is, the target item detection unit 210 may detect tumor cell, lymphocyte, macrophages, dendritic cell, fibroblast, endothelial cell, blood vessel, cancer stroma, cancer epithelium, cancer area, normal area (e.g., normal lymph node architecture region), and the like, as the target item in the pathology slide image.

The ROI determination unit 220 may determine one or more ROIs in the pathology slide image. In this example, the ROI may include a region in which one or more target items are detected in the pathology slide image. For example, the ROI determination unit 220 may determine, as the region of interest, a patch including one or more target items from among a plurality of patches forming the pathology slide image. In an embodiment, the ROI determination unit 220 may determine one or more ROIs based on a detection result for one or more target items fora pathology slide image. For example, the ROI determination unit 220 may determine one or more ROIs including at least some regions in the pathology slide image that satisfy a condition associated with the one or more target items. Additionally or alternatively, upon input of the detection result for one or more target items for a pathology slide image and/or the pathology slide image to an ROT extraction model, the ROI determination unit 220 may determine the regions being output as one or more ROIs.

The immune phenotype determination unit 230 may generate the information associated with immune phenotype for one or more ROIs in the pathology slide image. In an embodiment, the immune phenotype determination unit 230 may determine the immune phenotype of one or more ROIs based on the detection result for one or more target items. For example, the immune phenotype determination unit 230 may determine whether the immune phenotype of one or more ROIs is immune inflamed, immune excluded, or immune desert, based on the detection result for one or more target items. In another embodiment, the immune phenotype determination unit 230 may calculate the immune phenotype score of one or more ROIs based on the detection result for one or more target items. For example, the immune phenotype determination unit 230 may calculate a score for immune inflamed of one or more ROIs, a score for immune excluded, and/or a score for immune desert, based on the detection result for one or more target items. To this end, the immune phenotype determination unit 230 may calculate a score indicating a probability that the immune phenotype of one or more ROIs is immune inflamed, a score indicating a probability that it is immune excluded, and/or a score indicating a probability that it is immune desert.

In another embodiment, the immune phenotype determination unit 230 may generate a feature associated with one or more immune phenotypes for one or more ROIs, in this example, the feature associated with one or more immune phenotypes may include at least one of a statistical value or a vector associated with the immune phenotype. For example, the feature associated with one or more immune phenotypes may include score values related to the immune phenotype output from an artificial neural network model or a machine learning model. That is, it may include score values output in the process of determining the immune phenotype for one or more ROIs. As another example, the feature associated with one or more immune phenotypes may include a density value, number, or various statistics of immune cells corresponding to a threshold (or cut-off) for an immune phenotype or a vector value or the like expressing the distribution of immune cells.

As another example, the feature associated with one or more immune phenotypes may include a scalar value or a vector value including a relative relationship (e.g., a histogram vector or a graph expression vector considering the direction and distance) or relative statistics (e.g., the ratio of the number of immune cells to the number of specific cells, and the like) between an immune cell or cancer cell and a specific cell (e.g., cancer cells, immune cells, fibroblasts, lymphocytes, plasma cells, macrophage, endothelial cells, and the like). As another example, the feature associated with one or more immune phenotypes may include scalar values or vector values including statistics (e.g., the ratio of the number of immune cells to the cancer stromal region, and the like) or distributions (e.g., histogram vector or graph representation vector, and the like) of immune cells or cancer cells in a specific region (e.g., cancer area, cancer stromal region, tertiary lymphoid structure, normal region, necrosis, fat, blood vessel, high endothelial venule, lymphatic vessel, nerve, and the like).

As another example, the feature associated with one or more immune phenotypes may include scalar values or vector values including relative relationship (e.g., histogram vector or graph expression vector considering the direction and distance) or relative statistics (e.g., the ratio of the number of immune cells to the number of specific cells, and the like) between positive/negative cells according to the expression amount of the biomarker and the specific cells (e.g., cancer cells, immune cells, fibroblasts, lymphocytes, plasma cells, macrophage, endothelial cells, and the like). As another example, the feature associated with one or more immune phenotypes may include scalar values or vector values including statistics (e.g., the ratio of the number of immune cells to the cancer stromal region, and the like) or distributions (e.g., histogram vector or graph representation vector, and the like) of positive/negative cells according to the expression amount of the biomarker in a specific region (e.g., cancer area, cancer stromal region, tertiary lymphoid structure, normal region, necrosis, fat, blood vessel, high endothelial venule, lymphatic vessel, nerve, and the like).

In FIG. 2, the information processing system 100 includes the target item detection unit 210, the ROI determination unit 220, and the immune phenotype determination unit 230, but embodiments are not limited thereto, and some components may be omitted or other components may be added. In an embodiment, the information processing system 100 may further include a response predicting unit (not illustrated) for immune checkpoint inhibitor, and this response prediction unit for immune checkpoint inhibitor may generate a prediction result for whether the patient responds to the immune checkpoint inhibitor or not based on the information associated with immune phenotype. In another embodiment, the information processing system 100 may further include an output unit (not illustrated), and this output unit may output at least one of a detection result for the one or more target items, an immune phenotype of one or more ROIs, a prediction result as to whether or not the patient responds to immune checkpoint inhibitor, or a density of immune cells in each of one or more ROIs.

Figure 3:
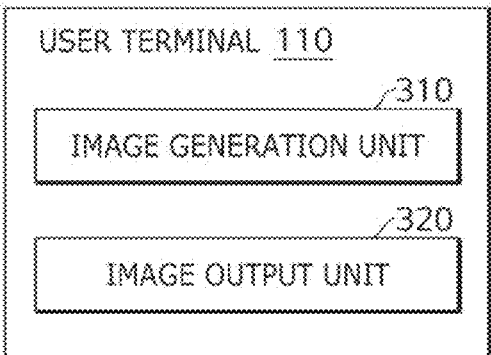
FIG. 3 is a block diagram illustrating an internal configuration of a user terminal according to an embodiment of the present disclosure.

FIG. 3 is a block diagram illustrating an internal configuration of the user terminal 110 according to an embodiment of the present disclosure. According to an embodiment, as illustrated, the user terminal 110 may include an image generation unit 310 and an image output unit 320. Respective components of the user terminal 110 illustrated in FIG. 3 represent functional components that can be divided on the basis of functions, and in an actual physical environment, a plurality of components may be implemented as being incorporated with each other.

The image generation unit 310 may obtain the information associated with immune phenotype for one or more ROIs in the pathology slide image. For example, the image generation unit 310 may receive the information associated with immune phenotype for one or more ROIs generated by the information processing system. Additionally or alternatively, as the user terminal 110 generates the information associated with immune phenotype for one or more ROIs, the image generation unit 310 may obtain the in formation associated with immune phenotype for one or more ROIs. Additionally or alternatively, the image generation unit 310 may receive the information associated with immune phenotype for one or more ROIs stored in an internal and/or external device of the user terminal 110.

The image generation unit 310 may generate an image indicative of the information associated with immune phenotype based on the information associated with immune phenotype for one or more ROIs. In an embodiment, when obtaining the immune phenotype of one or more ROIs, the image generation unit 310 may generate an image including a visual representation corresponding to the immune phenotype of one or more ROIs. In another embodiment, when receiving one or more immune phenotype scores for one or more ROIs, the image generation unit 310 may generate an image including a visual representation corresponding to one or more immune phenotype scores.

In another embodiment, the image generation unit 310 may generate an image including a visual representation corresponding to a feature (e.g., a value of a feature) associated with one or more immune phenotypes. For example, it is possible to generate an image including a heatmap according to the expression rate of a biomarker, a classification map classified based on a specific threshold (e.g., cut-off), and the like. In this example, the classification map may include a map visualizing a result of classifying a tumor proportion score (TPS) and/or a combined proportion score (CPS), which are information related to the expression of PD-L1, based on a specific threshold.

The image output unit 320 may output through the display device an image indicative of the information associated with immune phenotype. In an embodiment, the image output unit 320 may output through the display device one or more ROIs in the pathology slide image and an image including a visual representation. Alternatively, the image output unit. 320 may overlay an image including a visual representation on one or more ROIs in the pathology slide image.

FIG. 3 illustrates that the image generation unit 310 is included in the user terminal 110, but embodiments are not limited thereto, and the image generation unit 310 may be included in any external device (e.g., in the information processing system 100, and the like) capable of communicating with the user terminal 110 by wire and/or wirelessly. According to this configuration, the image output unit 320 of the user terminal 110 may receive an image generated from the external device, and display the received image on a display device connected to the user terminal 110 by wire and/or wirelessly.

In addition. FIGS. 2 and 3 illustrate that the target item detection unit 210, the ROI determination unit 220, the immune phenotype determination unit 230, the image generation unit 310, and the image output unit 320 are separately executed in the information processing system 100 and the user terminal 110, but embodiments are not limited thereto, and these components may be executed by one device. In another embodiment, these components may be distributed and processed in any combination by a plurality of any devices (e.g., the information processing system 100, the user terminal 110, and the like).

Figure 4:
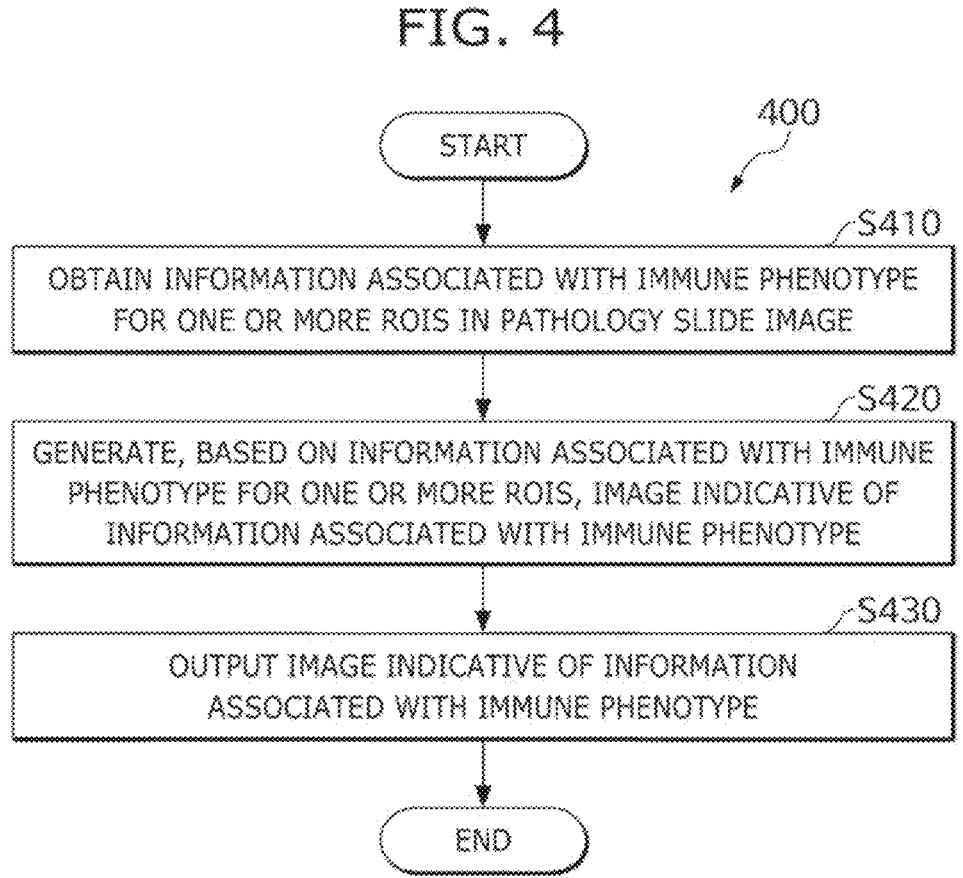
FIG. 4 is a flowchart illustrating a method for providing information associated with immune phenotype for pathology slide image according to an embodiment of the present disclosure.

FIG. 4 is a flowchart illustrating a method 400 for providing information associated with immune phenotype for pathology slide image according to an embodiment of the present disclosure. In an embodiment, the method 400 for providing information associated with immune phenotype for pathology slide image may be performed by a processor (e.g., at least one processor of the user terminal and/or at least one processor of the information processing system). The method 400 for providing information associated with immune phenotype for pathology slide image may be initiated by the processor obtaining the information associated with immune phenotype for one or more ROIs in the pathology slide image (S410). In this example, the information associated with immune phenotype for one or more ROIs may include an immune phenotype for one or more ROIs (e.g., at least one of immune inflamed, immune excluded, or immune desert), and/or an immune phenotype score (e.g., at least one of a score for immune inflamed, a score for immune excluded, or a score for immune desert) for one or more ROIs. Additionally or alternatively, the information associated with immune phenotype for one or more ROIs may include a feature associated with one or more immune phenotypes for one or more ROIs (e.g., statistical value or vector associated with the immune phenotype).

In an embodiment, the one or more ROIs may be determined based on a detection result for one or more target items for a pathology slide image. For example, the one or more ROIs may include at least some regions in the pathology slide image that satisfy a condition associated with the one or more target items. As another example, the one or more ROIs may be the regions being output upon input of the detection result for one or more target items for the pathology slide image and/or the pathology slide image to the ROI extraction model. In this case, the ROI extraction model may correspond to a model that is trained to output a reference ROI upon input of the detection result for one or more target items for reference pathology slide image (e.g., a reference pathology slide image including the detection result for target item), and/or a reference pathology slide image.

The processor may generate an image indicative of information associated with immune phenotype based on the information associated with immune phenotype for one or more ROIs (S420). In an embodiment, the processor may generate an image including a visual representation corresponding to immune phenotype of one or more ROIs. In another embodiment, the processor may generate an image including a visual representation corresponding to one or more immune phenotype scores. For example, the processor may generate an image including a visual representation corresponding to a score for immune inflamed. As another example, the processor may generate an image including a visual representation corresponding to a score for immune excluded. As another example, the processor may generate an image including a visual representation corresponding to a score for immune desert. In still another embodiment, the processor may generate an image including a visual representation corresponding to a feature associated with one or more immune phenotypes. For example, the processor may generate an image including a visual representation corresponding to a value of a feature associated with one or more immune phenotypes.

Then, the processor may output an image indicative of the information associated with immune phenotype (S430). In an embodiment, the processor may output one or more ROIs in the pathology slide image together with an image including a visual representation. In another embodiment, the processor may overlay an image including a visual representation on one or more ROIs in the pathology slide image.

In an embodiment, the processor may obtain a detection result for one or more target items from the pathology slide image, and generate an image indicative of the detection result for one or more target items. Then, the processor may output the image indicative of the detection result for one or more target items.

Figure 5:
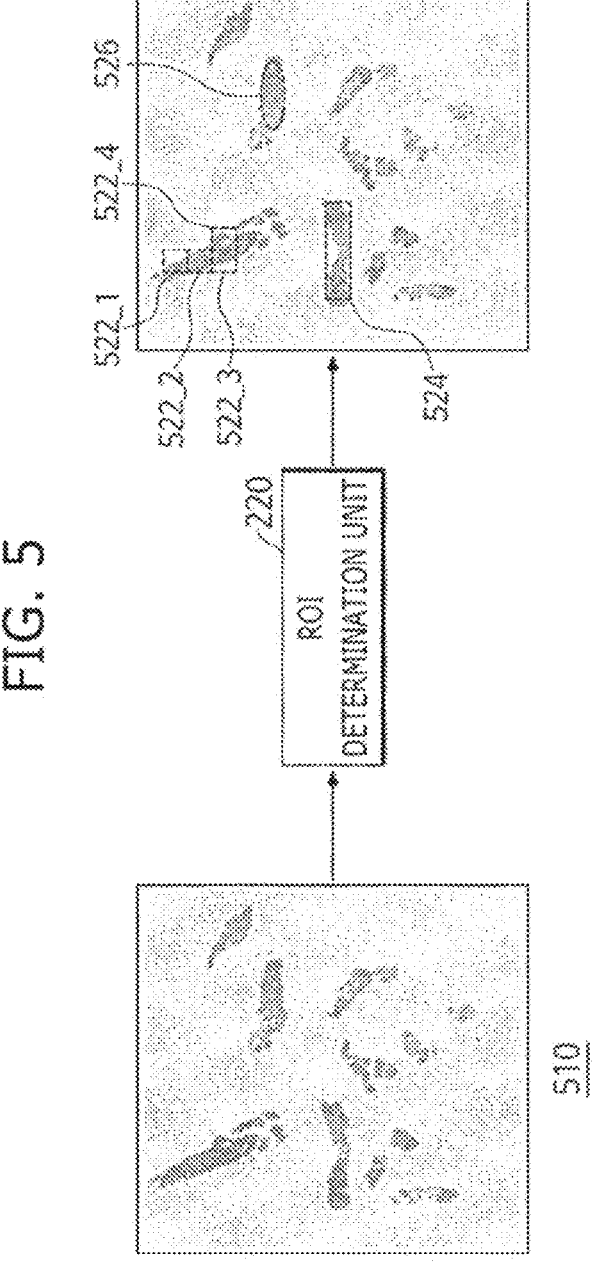
FIG. 5 is a diagram illustrating an example of determining one or more ROIs in a pathology slide image according to an embodiment of the present disclosure.

FIG. 5 is a diagram illustrating an example of determining one or more ROIs 522_1, 522_2, 522_3, 522_4, 524, and 526 in a pathology slide image 510 according to an embodiment of the present disclosure. To predict whether or not a patient will respond to immune checkpoint inhibitor, a user (e.g., a doctor, a researcher, and the like) may obtain a patient's tissue (e.g., tissue immediately prior to treatment, tissue after treated with immune checkpoint inhibitor, and the like) and generate one or more pathology slide images. For example, the user may perform H&E staining on the obtained patient's tissue and digitize the H&E-stained tissue slide through a scanner to generate a pathology slide image. As another example, the user may perform IHC staining on the obtained patient's tissue and digitize the IHC-stained tissue slide through a scanner to generate a pathology slide image.

The ROI determination unit 220 of the information processing system may determine one or more ROIs in the pathology slide image. In this example, the ROIs may correspond to the regions having various shapes, such as circle, square, rectangle, polygon, contour, and the like. In an embodiment, the ROT determination unit 220 may determine one or more ROIs based on the detection result for one or more target items for a pathology slide image. For example, among a plurality of patches (e.g., 1 mm² sized patches) generated by dividing the pathology slide image into N grids (where N is any natural number), the ROI determination unit 220 may determine a patch, from which one or more target items (e.g., items and/or immune cells associated with a cancer) are detected, as the ROI.

In an embodiment, the ROI determination unit 220 may determine one or more ROIs such that the ROIs include at least some regions in the pathology slide image that satisfy a condition associated with one or more target items. For example, the ROI determination unit 220 may determine a region, which has the number and/or area of target items (e.g., tumor cells, immune cells, cancer area, cancer stroma, and the like) equal to or greater than a reference value in the pathology slide image, as the ROI. Additionally or alternatively, the ROI determination unit 220 may determine a region, which has a numerical value such as a ratio, a density, and the like of the target item equal to or greater than a reference value in the pathology slide image, as the ROI. In this example, the target item may correspond to a cell and/or region detected to determine the immune phenotype. In addition, the reference value may refer to a numerical value set for the target item to define a statistically significant immune phenotype and/or a clinically significant immune phenotype.

In this case, the ROT determination unit 220 may determine a region, which has any area in the pathology slide image, as the ROI. For example, the area of the ROT may be dynamically determined to satisfy the condition associated with one or more target items described above. That is, the area of the ROI is not fixedly predetermined, and may be dynamically determined as the ROI determination unit 200 determines the region, which has the number, area, ratio, and/or density and the like of the target items equal to or greater than the reference value, as the ROI. Alternatively, the ROI determination unit 220 may determine one or more ROIs such that the area of the ROIs has a statically predetermined value.

In another embodiment, upon input of the detection result for one or more target items for the pathology slide image and/or the pathology slide image to an ROI extraction model, the ROI determination unit 220 may determine the regions being output as one or more ROIs. In this example, the ROI extraction model may correspond to a machine learning model (e.g., Neural Network, CNN, SVM, and the like) trained to output a reference ROI upon input of a detection result for one or more target items for reference pathology slide image and/or a reference pathology slide image. Even in this case, the area of the ROI may be determined dynamically and/or statically.

In an embodiment, when a plurality of ROIs are determined for the pathology slide image, the ROI determination unit 220 may determine the plurality of ROIs such that at least some of the plurality of ROIs overlap with each other. For example, when the ROT determination unit 220 determines a first ROT and a second ROI for the pathology slide image, at least some regions of the first ROI and at least some regions of the second ROI may be regions overlapping with each other. In another embodiment, when a plurality of ROIs for one pathology slide image is determined, the ROI determination unit 220 may determine the plurality of ROIs such that at least some of the plurality of ROIs do not overlap with each other.

As illustrated, the ROI determination unit 220 may receive the pathology slide image 510 (e.g., pathology slide image including a detection result for target item), and determine one or more ROIs in the pathology slide images 522_1, 522_2, 522_3, 522_4, 524, and 526. For example, the ROI determination unit 220 may determine the regions 522_1, 522_2, 522_3 and 522_4, which have a specific area (e.g., 1 mm² as a predetermined area) that satisfies the condition associated with the target item, as the ROIs. As another example, the ROI determination unit 220 may determine a region 524, which satisfies the condition associated with the target item, as the ROI, and the area of the ROI may be dynamically determined. As still another example, the ROI determination unit 220 may determine an elliptical region 526, which satisfies the condition associated with the target item, as the ROT.

Figure 6:
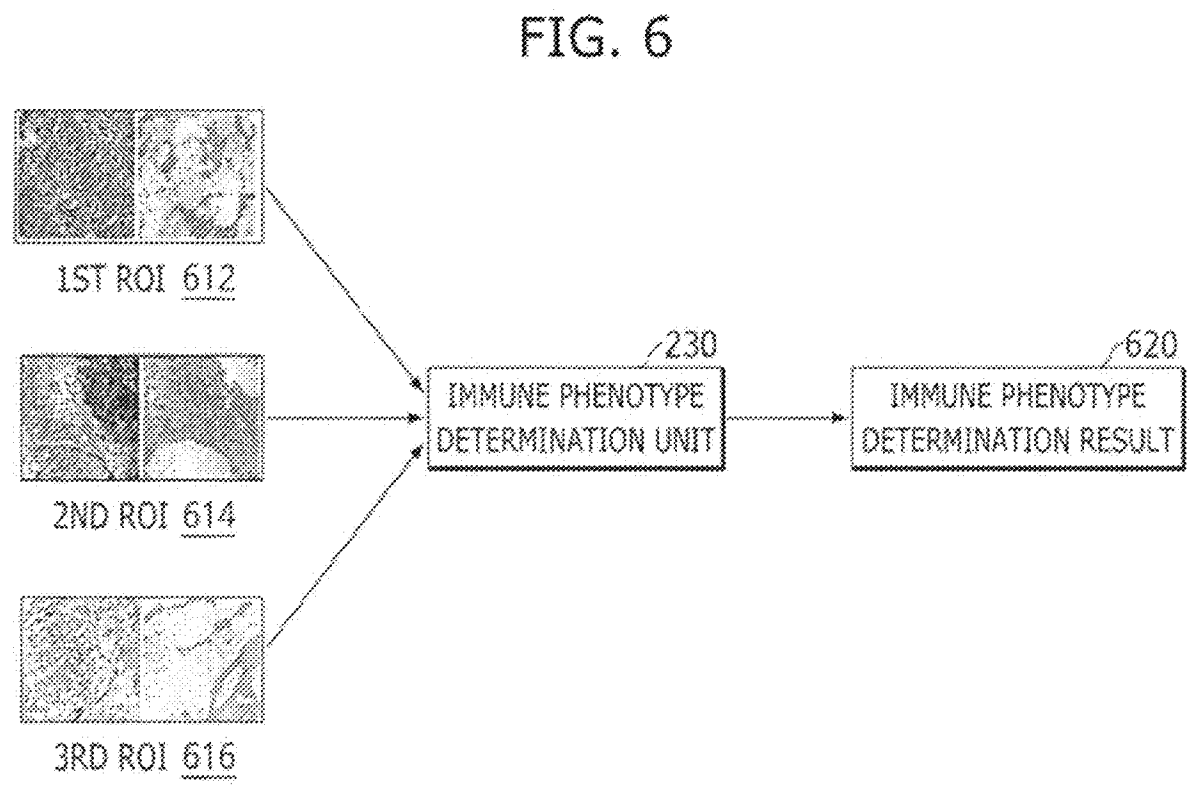

FIG. 6 is a diagram illustrating an example of generating an immune phenotype determination result 620 according to an embodiment of the present disclosure. In an embodiment, the immune phenotype determination unit 230 may generate the immune phenotype determination result 620 of one or more ROIs based on the detection result for one or more target items (e.g., items and/or immune cells associated with a cancer) in the one or more ROIs. For example, the immune phenotype determination unit 230 may determine the immune phenotype of the corresponding ROI as at least one of immune inflamed, immune excluded, or immune desert based on the detection result for one or more target items in one or more ROIs.

In another embodiment, the immune phenotype determination unit 230 may calculate an immune phenotype score for one or more ROIs based on the detection result for one or more target items in one or more ROIs. For example, the immune phenotype determination unit 230 may calculate at least one of a score for immune inflamed, a score for immune excluded, or a score for immune desert in the corresponding ROI based on the detection result for one or more target items in one or more ROIs. In this case, the immune phenotype determination unit 230 may determine an immune phenotype of the corresponding ROT based on at least one of a score for immune inflamed, a score for immune excluded, and a score for immune desert for one or more ROIs. For example, when the score for immune inflamed of a specific ROI is equal to or greater than a threshold value, the immune phenotype determination unit 230 may determine the immune phenotype of the corresponding ROI as immune inflamed.

In an embodiment, the immune phenotype determination unit 230 may calculate at least one of the number, distribution, or density of target items in one or more ROIs, and may determine an immune phenotype and/or an immune phenotype score of one or more ROIs based on at least one of the calculated number, distribution, or density of the immune cells. For example, the immune phenotype determination unit 230 may calculate, within one or more ROIs, a density of lymphocytes in the cancer area and a density of lymphocytes in the cancer stroma area, and determine the immune phenotype of the one or more ROIs based on at least one of the density of immune cells in the cancer area or the density of immune cells in the cancer stroma. Additionally or alternatively, the immune phenotype determination unit 230 may determine the immune phenotype of one or more ROIs as one of immune inflamed, immune excluded, or immune desert, by referring to the number of immune cells included in the specific region in the cancer area.

For example, the immune phenotype determination unit 230 may determine the immune phenotype of a first ROI 612, which has a density of immune cells in the cancer area equal to or greater than a first threshold density, as immune inflamed. In addition, the immune phenotype determination unit 230 may determine the immune phenotype of a second ROI 614, which has a density of immune cells in the cancer area less than the first threshold density and a density of immune cells in the cancer stroma equal to or greater than the second threshold density, as immune excluded. In addition, the immune phenotype determination unit 230 may determine the immune phenotype of a third ROI 616 having a density of immune cells in the cancer area less than the first threshold density and having a density of immune cells in the cancer stroma less than the second threshold density is immune desert. In this example, the first threshold density may be determined based on a distribution of the density of the immune cells in the cancer area in each of a plurality of ROIs in the plurality of pathology slide images. Likewise, the second threshold density may be determined based on a distribution of the density of the immune cells in the cancer stroma in each of the plurality of ROIs in the plurality of pathology slide images.

In another embodiment, the immune phenotype determination unit 230 may input the feature for each of the one or more ROIs to the artificial neural network immune phenotype classification model to determine the immune phenotype and/or immune phenotype score of each of the one or more ROIs. In this example, the artificial neural network immune phenotype classification model may correspond to a classifier that is trained to determine the immune phenotype of the reference ROI as one of immune inflamed, immune excluded, or immune desert upon input of the feature for the reference ROI. In addition, in this example, the feature for each of one or more ROIs may include a statistical feature for one or more target items in each of one or more ROIs (e.g., density, number, and the like, of specific target items in the RON), a geometric feature for one or more target items (e.g., a feature including relative position information between specific target items, and the like), and/or an image feature, and the like corresponding to each of the one or more ROIs (e.g., a feature extracted from a plurality of pixels included in the ROIs, an image vector corresponding to the ROIs, and the like). Additionally or alternatively, the feature for each of the one or more ROIs may include a feature obtained by concatenating two or more features from among the statistical feature for one or more target items in each of the one or more ROIs, the geometric feature for the one or more target items, or the image feature corresponding to each of the one or more ROIs.

As illustrated, the immune phenotype determination unit 230 may receive one or more ROIs 612, 614, and 616, and generate the immune phenotype determination result 620. In this example, one or more ROIs 612, 614, and 616 may include the detection result for target item for the corresponding ROI. Accordingly, the immune phenotype determination unit 230 may generate the immune phenotype determination result 620 for the ROI that includes the detection result for target item. For example, the immune phenotype determination unit 230 may generate the immune phenotype determination result 620 including the immune phenotype of the corresponding ROI and/or the immune phenotype score of the corresponding ROI, The generated immune phenotype determination result 620 and/or one or more ROIs 612, 614, and 616 may be provided to the user terminal.

Figure 7:
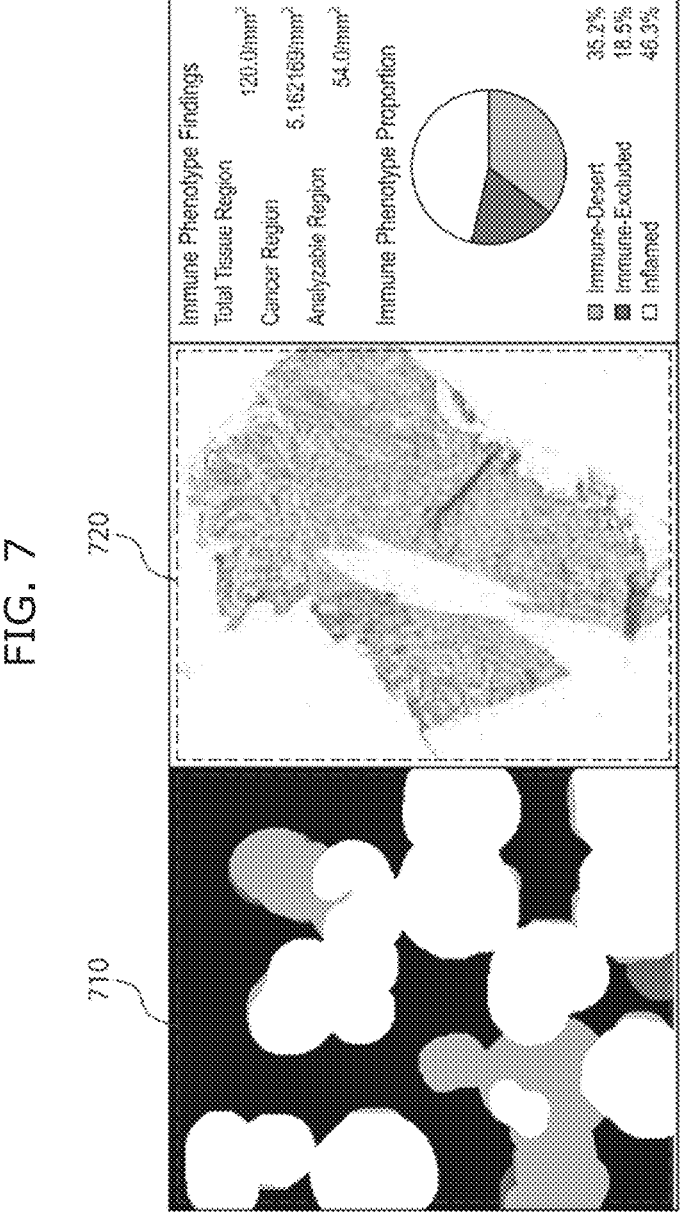
FIG. 7 is a diagram illustrating an example of outputting the immune phenotype determination result according to an embodiment.

FIG. 7 is a diagram illustrating an example of outputting the immune phenotype determination result according to an embodiment of the present disclosure. As the information processing system (e.g., at least one processor of the information processing system) provides the user terminal with information associated with immune phenotype for one or more ROIs in the pathology slide image, the user terminal may output the received information through an output device to provide it to the user. In this example, the information associated with immune phenotype for one or more ROIs may include the immune phenotype score for one or more ROIs. The user terminal (e.g., at least one processor of the user terminal) may output an image indicative of the information associated with immune phenotype for one or more ROIs.

To this end, the user terminal may generate an image including a visual representation corresponding to one or more immune phenotype scores for one or more ROIs. For example, in a region corresponding to one or more ROIs, the user terminal may generate an image including a visual representation corresponding to one or more immune phenotype scores for the ROI. In this example, the one or more immune phenotype scores may include at least one of a score for immune inflamed, a score for immune excluded, or a score for immune desert. In addition, the visual representation may include color (e.g., color, brightness, saturation, and the like), text, image, mark, figure, and the like.

For example, with respect to the score for immune inflamed (that is, the immune inflamed score), the user terminal may generate an image including a color with higher saturation for a region corresponding to ROI having a higher immune inflamed score, and generate an image including a color with lower saturation for a region corresponding to ROT having a lower immune inflamed score. As another example, with respect to the score for the immune inflamed, the user terminal may generate an image including a first visual representation in a region corresponding to the ROI having the immune inflamed score corresponding to a first score section, including a second visual representation in a region corresponding to the ROI having the immune inflamed score corresponding to a second score section, and including a third visual representation in a region corresponding to the ROI having the immune in flamed score corresponding to a third score section. In this example, the first visual representation, the second visual representation, and the third visual representation may be different from each other.

In an embodiment, the user terminal may output one or more ROIs in the pathology slide image together with an image including a visual representation. For example, the user terminal may simultaneously display the image (e.g., the image including a visual representation) generated as described above and at least some regions of the pathology slide image (e.g., the region corresponding to the generated image) on a display device. In another embodiment, the user terminal may overlay the image including the visual representation on one or more ROIs in the pathology slide image. For example, the user terminal may overlap the image (e.g., the image including a visual representation) generated as described above on at least some regions of the pathology slide image (e.g., the region corresponding to the generated image), and display on the display device.

For example, as illustrated, the user terminal may generate an image 710 in which the region corresponding to the ROI having the immune inflamed score falling in the first score section is displayed in white, the region corresponding to the ROI having the immune inflamed score falling in the second score section is displayed in light gray, the region corresponding to the ROI having the immune inflamed score falling in the third score section is displayed in dark gray, and the regions other than the ROIs are displayed in black. Then, the user terminal may arrange, in parallel, the image 710 including a visual representation and a region 720 in the pathology slide image which corresponds to the generated image 710, and display them together on the user interface.

Additionally or alternatively, the user terminal may further display on the user interface the information associated with immune phenotype, such as text, numerical values, graphs, and the like for a "total tissue region" (e.g., a tissue region in a pathology slide image), a "cancer region" (e.g., a cancer area in a pathology slide image, an "analyzable region" (e.g., an ROT in pathology slide image), and an "immune phenotype proportion" (e.g., immune phenotype proportion). Additionally or alternatively, a region in the pathology slide images, which is displayed on the display device, may include the detection result for one or more target items for the corresponding region. That is, when outputting an image of at least some regions of the pathology slide image, the user terminal may output an image of at least some regions displaying the detection results for one or more target items through the display device.

Figure 8:
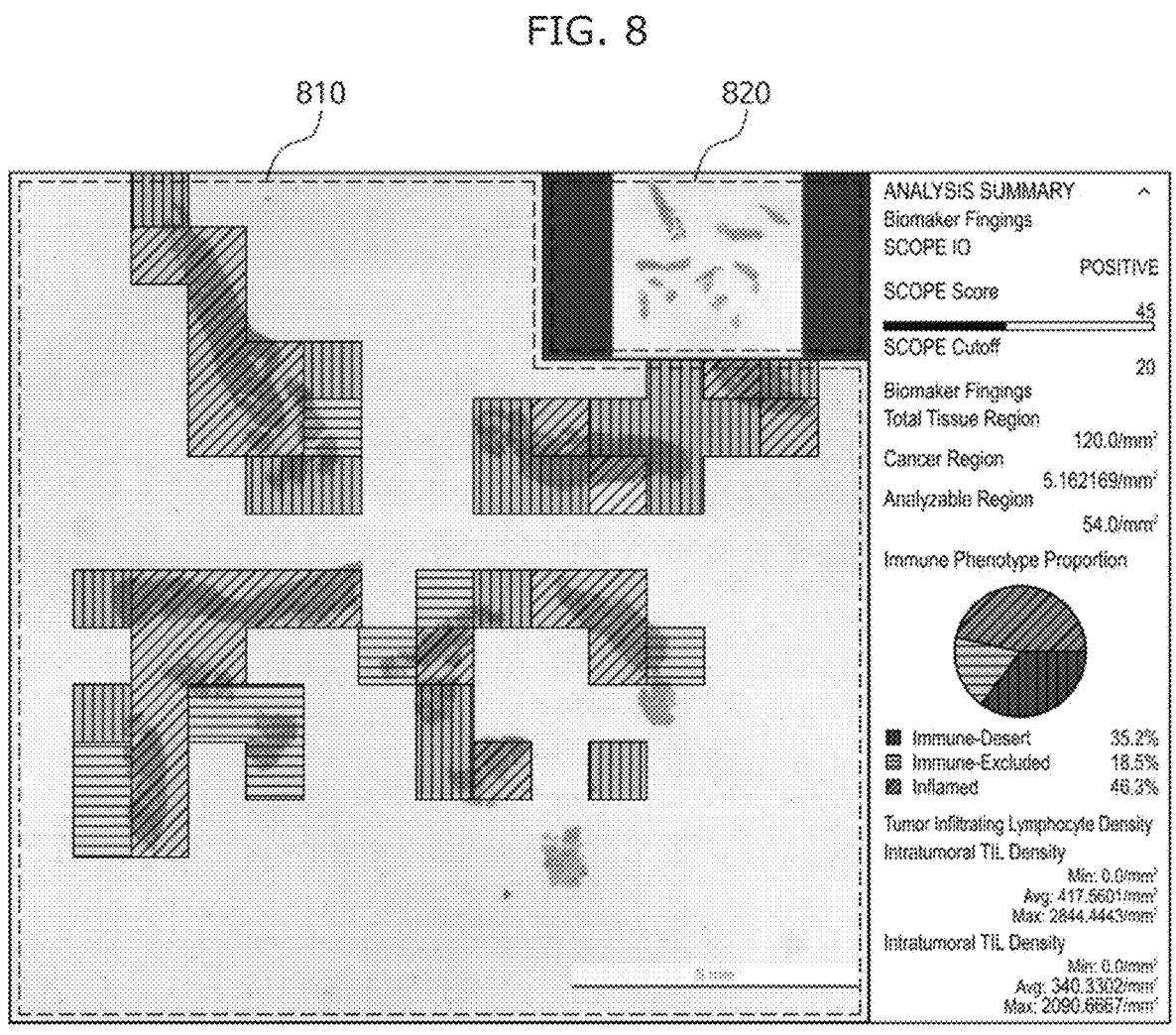
FIG. 8 is a diagram illustrating an example of outputting an immune phenotype determination result according to an embodiment of the present disclosure.

FIG. 8 is a diagram illustrating an example of outputting an immune phenotype determination result according to an embodiment of the present disclosure. In an embodiment, the information associated with immune phenotype for one or more ROIs obtained by the user terminal (e.g., at least one processor of the user terminal) may include the immune phenotypes of the one or more ROIs. For example, the user terminal may output an image indicative of the information associated with immune phenotype for one or more ROIs.

To this end, the user terminal may generate an image including a visual representation corresponding to the immune phenotype of one or more ROIs. For example, the user terminal may generate an image including a visual representation corresponding to the immune phenotype of the corresponding ROI in a region corresponding to one or more ROIs. That is, an image may be generated, which includes the first visual representation in a region corresponding to the ROT having the immune phenotype of immune inflamed, includes the second visual representation in a region corresponding to the ROT having the immune phenotype of immune excluded, and includes the third visual representation in a region corresponding to the ROI having the immune phenotype of immune desert. In this case, the visual representation may include color (e.g., color, brightness, saturation, and the like), text, image, mark, figure, and the like, to distinguish each immune phenotype. For example, the first visual representation indicating immune inflamed may be red color, the second visual representation indicating immune excluded may be green color, and the third visual representation indicating immune desert may be blue color. Additionally or alternatively, the first visual representation indicating immune inflamed may be a circle mark, the second visual representation indicating immune excluded may be a triangle mark, and the third visual representation indicating immune desert may be an X mark.

In an embodiment, the user terminal may output one or more ROIs in the pathology slide image together with an image including the visual representation. For example, the user terminal may display the image (e.g., the image including a visual representation) generated as described above together with at least some regions of the pathology slide image (e.g., the region corresponding to the generated image) on the display device. In another embodiment, the user terminal may overlay the image including the visual representation on one or more ROIs in the pathology slide image. For example, the user terminal may overlap the image (e.g., the image including a visual representation) generated as described above transparently, translucently, or opaquely on at least some regions of the pathology slide image (e.g., the region corresponding to the generated image), and display on the display device.

For example, as illustrated, the user terminal may generate an image that includes a diagonal marker in a region corresponding to the ROI having the immune phenotype of immune inflamed, includes a vertical line marker in a region corresponding to the ROI having the immune phenotype of immune excluded, and includes a horizontal line marker in a region corresponding to the ROI having the immune phenotype of immune desert. Then, the user terminal may display on the user interface an image 810 including the image including a visual representation overlaid on a corresponding region of the pathology slide image. Additionally, the user terminal may also display on the user interface an image 820 of at least some regions of the pathology slide image (e.g., region corresponding to an image including a visual representation and/or the entire pathology slide image) separately (e.g., in a form of a minimap).

Additionally or alternatively, the user terminal may display on the user interface the information associated with immune phenotype, such as text, numerical values, graphs, and the like for "analysis summary", "biomarker findings", "score" (e.g., immune inflamed score, and the like), "cutoff" (e.g., reference value used in determining the immune phenotype, and the like), "total tissue region", "cancer region", "analyzable region", "immune phenotype proportion", "tumor infiltrating lymphocyte density" (e.g., immune cell density in the cancer area, immune cell density in the cancer stromal region, and the like). Additionally or alternatively, the region in the pathology slide images, which is displayed on the display device, may include the detection result for one or more target items for the corresponding region. That is, when outputting an image of at least some regions of the pathology slide image, the user terminal may output an image of at least some regions displaying the detection results for one or more target items through the display device.

Figure 9:
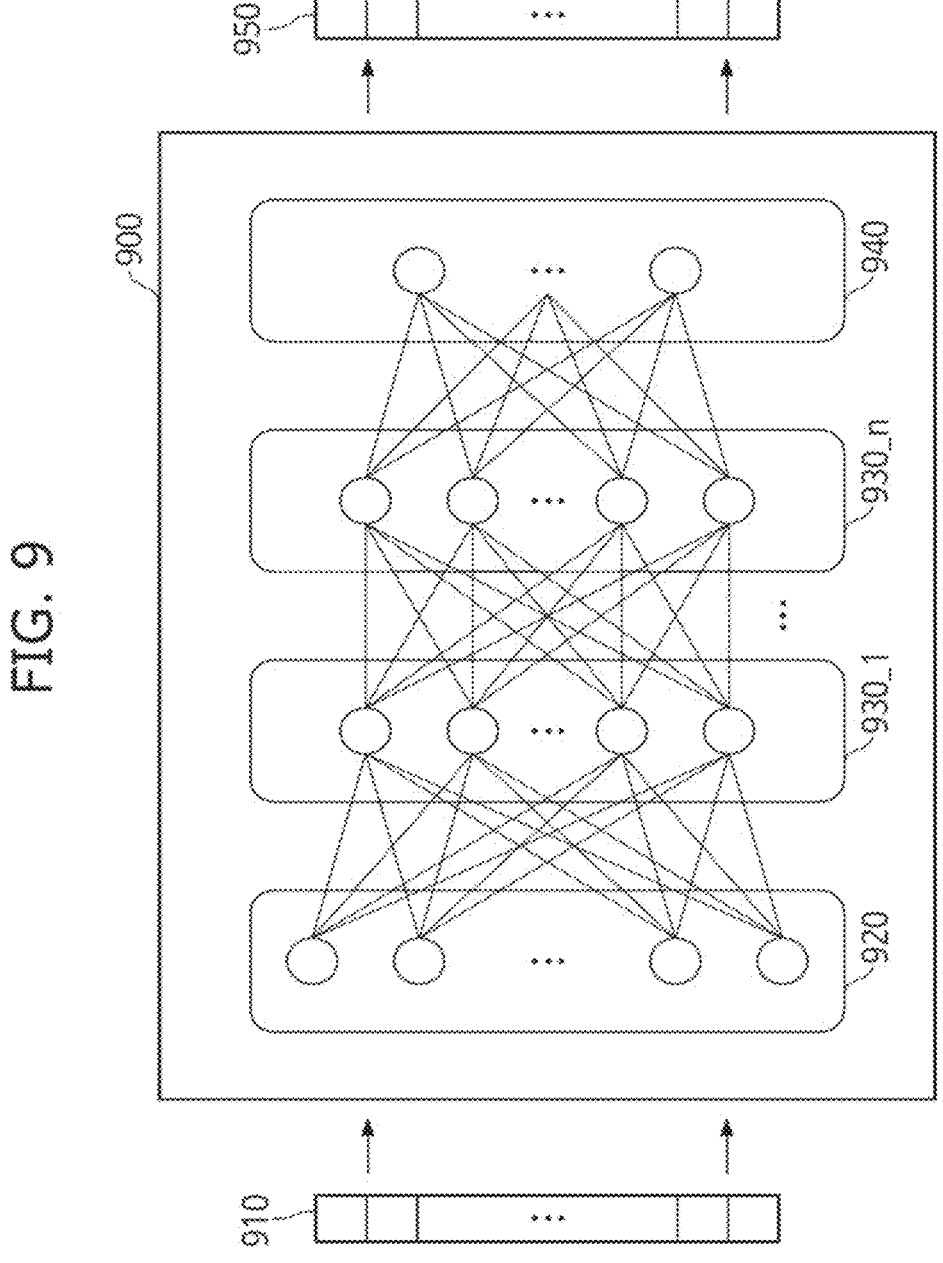
FIG. 9 is an exemplary diagram illustrating an artificial neural network model according to an exemplary embodiment.

FIG. 9 is an exemplary diagram illustrating an artificial neural network model 900 according to an embodiment of the present disclosure. In machine learning technology and cognitive science, an artificial neural network model 900 as an example of the machine learning model refers to a statistical learning algorithm implemented based on a structure of a biological neural network, or to a structure that executes such algorithm.

According to an embodiment, the artificial neural network model 900 may represent a machine learning model that obtains a problem solving ability by repeatedly adjusting the weights of synapses by the nodes that are artificial neurons forming the network through synaptic combinations as in the biological neural networks, thus training to reduce errors between a target output corresponding to a specific input and a deduced output. For example, the artificial neural network model 900 may include any probability model, neural network model, and the like, that is used in artificial intelligence learning methods such as machine learning and deep learning.

According to an embodiment, the artificial neural network model 900 may include an artificial neural network model configured to detect one or more target items from a pathology slide image being inputted. Additionally or alternatively, the artificial neural network model 900 may include an artificial neural network model configured to determine one or more ROIs from an input pathology slide image.

The artificial neural network model 900 is implemented as a multilayer perceptron (MLP) formed of multiple nodes and connections between them. The artificial neural network model 900 according to an embodiment may be implemented using one of various artificial neural network model structures including the MLP. As shown in FIG. 9, the artificial neural network model 90) includes an input layer 920 receiving an input signal or data 910 from the outside, an output layer 940 outputting an output signal or data 950 corresponding to the input data, and (n) number of hidden layers 930_1 to 930_n (where n is a positive integer) positioned between the input layer 920 and the output layer 940 to receive a signal from the input layer 920, extract the features, and transmit the features to the output layer 940. In an example, the output layer 940 receives signals from the hidden layers 930_1 to 930_n and outputs them to the outside.

The method of training the artificial neural network model 900 includes the supervised learning that trains to optimize for solving a problem with inputs of teacher signals (correct answer), and the unsupervised learning that does not require a teacher signal. In an embodiment, the information processing system may train the artificial neural network model 900 by supervised learning and/or unsupervised learning to detect one or more target items from a pathology slide image. For example, the information processing system may train the artificial neural network model 90 by supervised learning to detect one or more target items from the pathology slide image by using a reference pathology slide image and label information for one or more reference target items.

In another embodiment, the information processing system may train, the artificial neural network model 900 by supervised learning and/or unsupervised learning to determine one or more ROIs from the pathology slide image. For example, the information processing system may train the artificial neural network model 900 by supervised learning to determine one or more ROIs from the pathology slide image using the reference pathology slide image and/or the detection result for one or more target items for the reference pathology slide image (e.g., reference pathology slide image including the detection result for target item), and the label information on the reference ROI. In this example, the ROI and/or the reference ROI may include at least some regions in the pathology slide image and/or the reference pathology slide image that satisfy the condition associated with one or more target items.

The artificial neural network model 900 trained as described above may be stored in a memory (not illustrated) of the information processing system, and in response to an input for the pathology slide image received from the communication module and/or the memory, may detect one or more target items in the pathology slide image. Additionally or alternatively, the artificial neural network model 900 may determine one or more ROIs from the pathology slide image, in response to the detection result for the one or more target items for the pathology slide image and/or an input to the pathology slide image.

According to an embodiment, the input variable of the artificial neural network model for detecting the target item may be one or more pathology slide images (e.g., H&E-stained pathology slide images, IHC-stained pathology slide images). For example, the input variable input to the input layer 920 of the artificial neural network model 900 may be the image vector 910 which may be one or more pathology slide images configured as one vector data element. The output variable output from the output layer 940 of the artificial neural network model 900 in response to the input of the image may be a vector 950 representing or characterizing one or more target items detected in the pathology slide image. That is, the output layer 940 of the artificial neural network model 900 may be configured to output a vector representing or characterizing one or more target items detected from the pathology slide image. In the present disclosure, the output variable of the artificial neural network model 900 is not limited to the types described above, and may include any information/data indicative of one or more target items detected from the pathology slide image. In addition, the output layer 940 of the artificial neural network model 900 may be configured to output a vector indicative of the reliability and/or accuracy of the output detection result for target item and the like.

In another embodiment, the input variable of the machine learning model for determining the ROI, that is, the input variable of the artificial neural network model 900 may be the detection result for one or more target items for the pathology slide image (e.g., detection data for the target item in the pathology slide image) and/or the pathology slide image. For example, the input variable input to the input layer 920 of the artificial neural network model 900 may be the image vector 910 which may be the detection result for the one or more target items for the pathology slide image and/or the pathology slide image configured as one vector data element. An output variable output from the output layer 940 of the artificial neural network model 904) in response to input for the detection result for one or more target items for the pathology slide image and/or the pathology slide image may be the vector 950 that indicates or characterizes one or more ROIs. In the present disclosure, the output variable of the artificial neural network model 900 is not limited to the types described above, and may include any information/data indicative of one or more ROIs.

As described above, the input layer 920 and the output layer 940 of the artificial neural network model 900 are respectively matched with a plurality of output variables corresponding to a plurality of input variables, and the synaptic values between nodes included in the input layer 920, the hidden layers 930_1 to 930_n, and the output layer 940 are adjusted, so that by training, a correct output corresponding to a specific input can be extracted. Through this training process, the features hidden in the input variables of the artificial neural network model 900 may be confirmed, and the synaptic values (or weights) between the nodes of the artificial neural network model 900 may be adjusted so as to reduce the errors between the output variable calculated based on the input, variable and the target output. By using the artificial neural network model 900 trained in this way, in response to input of the pathology slide image, the detection result for target item may be output. Additionally or alternatively, by using the artificial neural network model 900, one or more ROIs may be output in response to input of the pathology slide image and/or the detection result for one or more target items for the pathology slide image (e.g., the pathology slide image including the detection result for target item).

Figure 10:
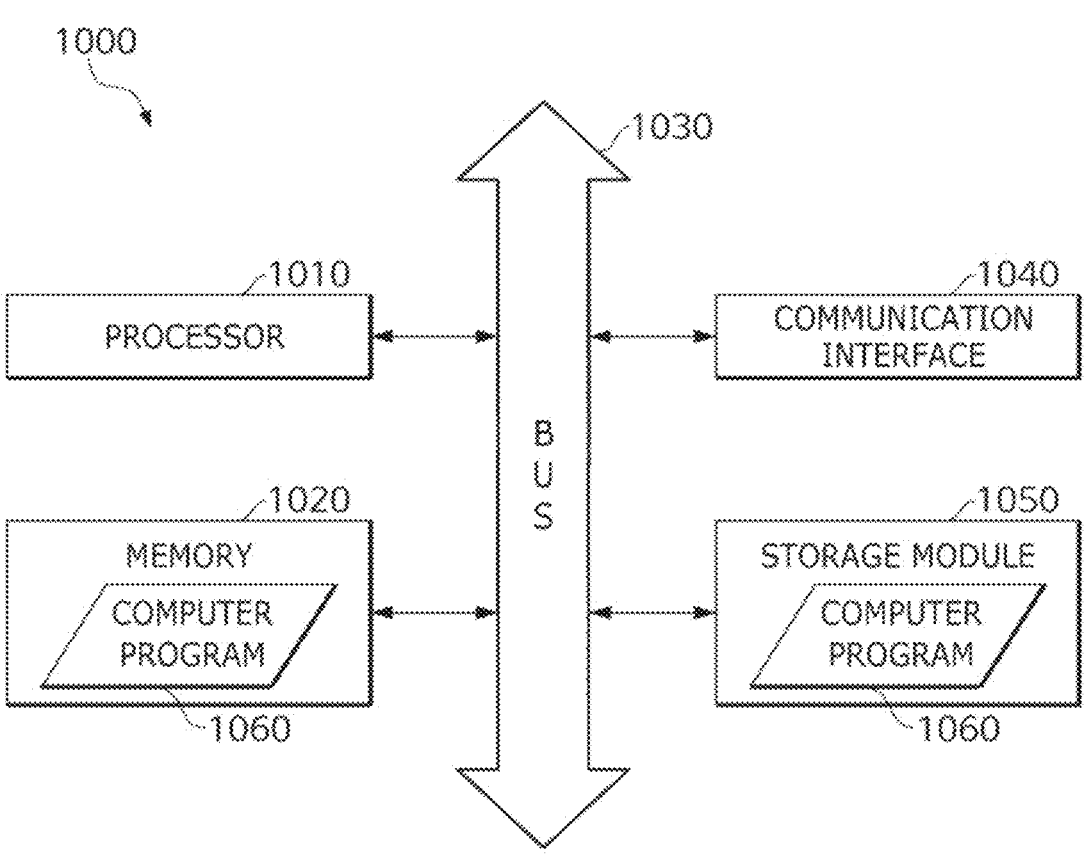
FIG. 10 is a configuration diagram of an exemplary computing device (e.g., user terminal) that provides information associated with immune phenotype for pathology slide image according to an embodiment.

FIG. 10 is a configuration diagram of an exemplary computing device 1000 (e.g., user terminal) that provides information associated with immune phenotype for pathology slide image according to an embodiment of the present disclosure. As illustrated, the computing device 1000 may include one or more processors 1010, a bus 1030, a communication interface 1040, a memory 1020 that loads a computer program 1060 executable by the processors 1010, and a storage module 1050 storing the computer program 1060. However, only the components related to the embodiment of the present disclosure are illustrated in FIG. 10. Accordingly, those of ordinary skill in the art to which the present disclosure pertains will be able to recognize that other general-purpose components may be further included in addition to the components shown in FIG. 10.

The processors 1010 control the overall operation of components of the computing device 1000. The processors 1010 may be configured to include a central processing unit (CPU), a microprocessor unit (MPU), a micro controller unit (MCU), a graphic processing unit (GPU), or any type of processor well known in the technical field of the present disclosure. In addition, the processors 1010 may perform an arithmetic operation on at least one application or program for executing the method according to the embodiments of the present disclosure. The computing device 1000 may include one or more processors.

The memory 1020 may store various types of data, commands, and/or information. The memory 1020 may load one or more computer programs 1060 from the storage module 1050 in order to execute a method/operation according to various embodiments of the present disclosure. The memory 1020 may be implemented as a volatile memory such as RAM, but the technical scope of the present disclosure is not limited thereto.

The bus 1030 may provide a communication function between components of the computing device 1000. The bus 1030 may be implemented as various types of buses such as an address bus, a data bus, a control bus, or the like.

The communication interface 1040 may support wired/wireless Internet communication of the computing device 1000. In addition, the communication interface 1040 may support various other communication methods in addition to the Internet communication. To this end, the communication interface 1040 may be configured to include a communication module well known in the technical field of the present disclosure.

The storage module 1050 may non-temporarily store one or more computer programs 1060. The storage module 1050 may be configured to include a nonvolatile memory such as a read only memory (ROM), an erasable programmable ROM (EPROM), an electrically erasable programmable ROM (EEPROM), a flash memory, and the like, a hard disk, a detachable disk, or any type of computer-readable recording medium well known in the art to which the present disclosure pertains.

The computer program 1060 may include one or more instructions that, when loaded into the memory 1020, cause the processors 1010 to perform an operation/method in accordance with various embodiments of the present disclosure. That is, the processors 1010 may perform operations/methods according to various embodiments of the present disclosure by executing one or more instructions.

For example, the computer program 1060 may include one or more instructions for causing the following operations to be performed: obtaining information associated with immune phenotype for one or more ROIs in the pathology slide image; generating an image indicative of information associated with immune phenotype based on the information associated with immune phenotype for one or more ROIs; outputting the image indicative of the information associated with immune phenotype, and the like. In this case, a system for predicting a response to immune checkpoint inhibitor according to some embodiments of the present disclosure may be implemented through the computing device 1000.

Figure 11:
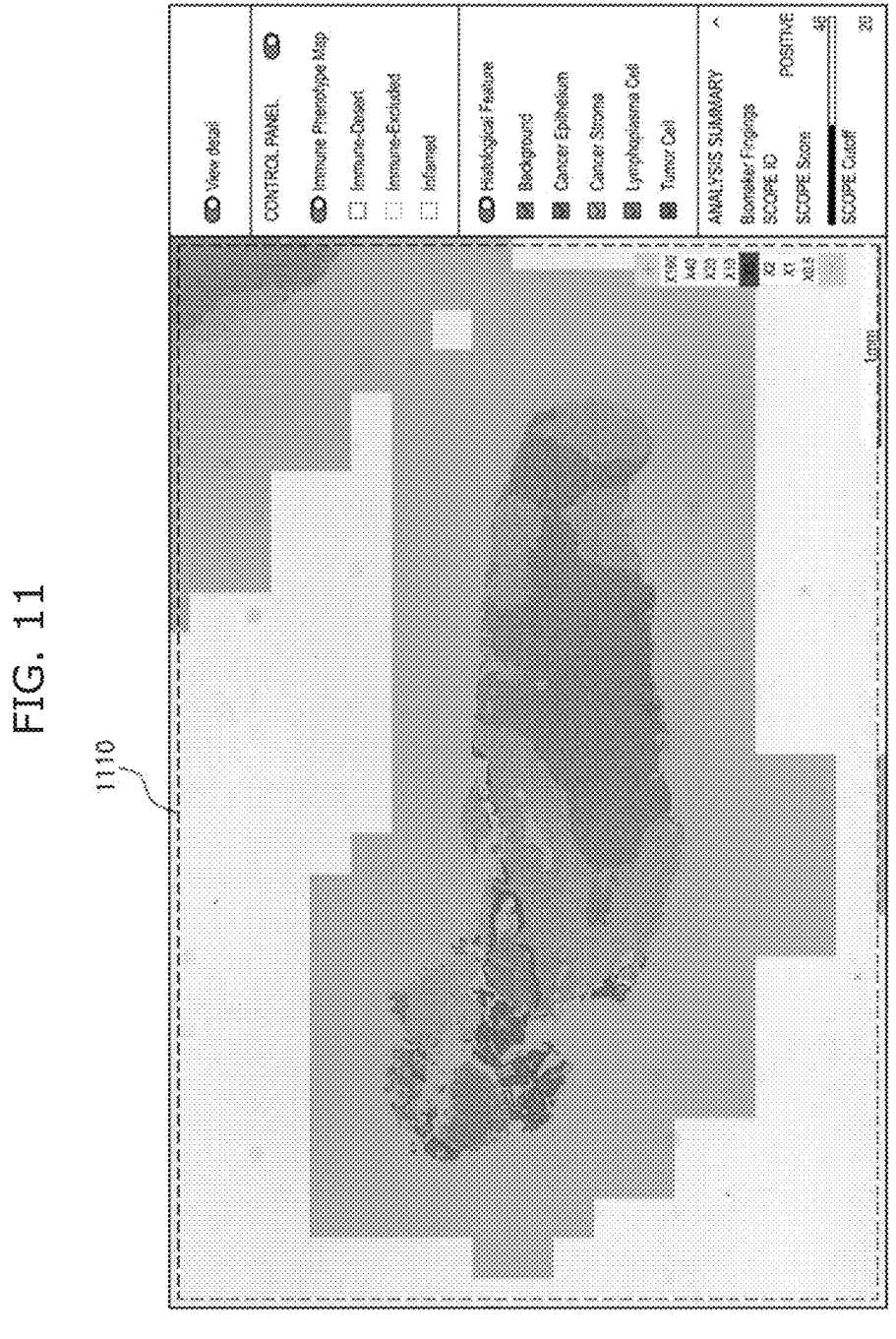
FIG. 11 is a diagram illustrating an example of outputting a detection result for target item according to an embodiment of the present disclosure.

FIG. 11 is a diagram illustrating an example of outputting a detection result for target item according to an embodiment of the present disclosure. The processor (e.g., at least one processor of the user terminal) may obtain a detection result for one or more target items from the pathology slide image. For example, the information processing system may use a target item detection model to detect one or more target items from the pathology slide image, and provide the detection result for target item to the user terminal. In this example, the target item detection model may include a model trained to detect one or more reference target items from the reference pathology slide image.

The processor may generate an image indicating the detection result for one or more target items, and output the generated image indicating the detection result for one or more target items. In an embodiment, the processor may generate and output an image including visual representations capable of distinguishing respective target items, based on the detection result for one or more target items from the pathology slide image. For example, the processor may generate an image including a visual representation indicating each of the target items (e.g., cancer area, cancer stromal region, blood vessel, cancer cell, immune cell, positive/negative cells according to the expression amount of the biomarker, and the like) that may be considered in determining the immune phenotype. Additionally or alternatively, based on the detection result for one or more target items, the processor may generate an image including a segmentation map for the target item in units of regions, a contour for the target item having a specific structure (e.g., a blood vessel, and the like), a center point of the target item in units of cells, or a contour indicative of the shape of the target item in units of cells, and the like.

In an embodiment, the processor may output one or more ROIs in the pathology slide image and an image indicative of the detection result for one or more target items for one or more ROIs. For example, the processor may output the image generated as described above (e.g., the image including a visual representation) together with at least some regions of the pathology slide image (e.g., region corresponding to the generated image). As another example, the processor may overlay the image indicative of the detection result for one or more target items (e.g., the image including a visual representation) on one or more ROIs in the pathology slide image. For example, the user terminal may overlap the image (e.g., the image including a visual representation) generated as described above on at least some regions of the pathology slide image (e.g., the region corresponding to the generated image), and display it on a display device connected to the user terminal.

For example, as illustrated, the processor may display on the user interface an image 1110 displaying a first color indicating a background other than the target item, a second color indicating a cancer epithelium area, a third color indicating a cancer stromal region, a fourth color indicating an immune cell (e.g., a central point of an immune cell), and a fifth color indicating a cancer cell (e.g., a center point of a cancer cell) on the corresponding regions of the pathology slide image. In this example, the image 1110 may correspond to an image obtained by overlaying (or merging) the image indicative of the detection result for one or more target items on a corresponding region of the pathology slide image. Further, the first color, the second color, the third color, the fourth color and/or the fifth color may correspond to different colors that can be distinguished from each other.

Additionally or alternatively, as the information associated with immune phenotype, the user terminal may display on the user interface visual representations corresponding to respective target items (e.g., color information corresponding to respective target items, and the like), text, numerical values, markers, graphs, and the like for "analysis summary". Additionally or alternatively, the user terminal may output a user interface through which the user can select a target item to be displayed with a visual representation in a corresponding region in the pathology slide image. In FIG. 11, color is used as an example of the visual representation to indicate the information associated with immune phenotype, but embodiments are not limited thereto.

Figure 12:
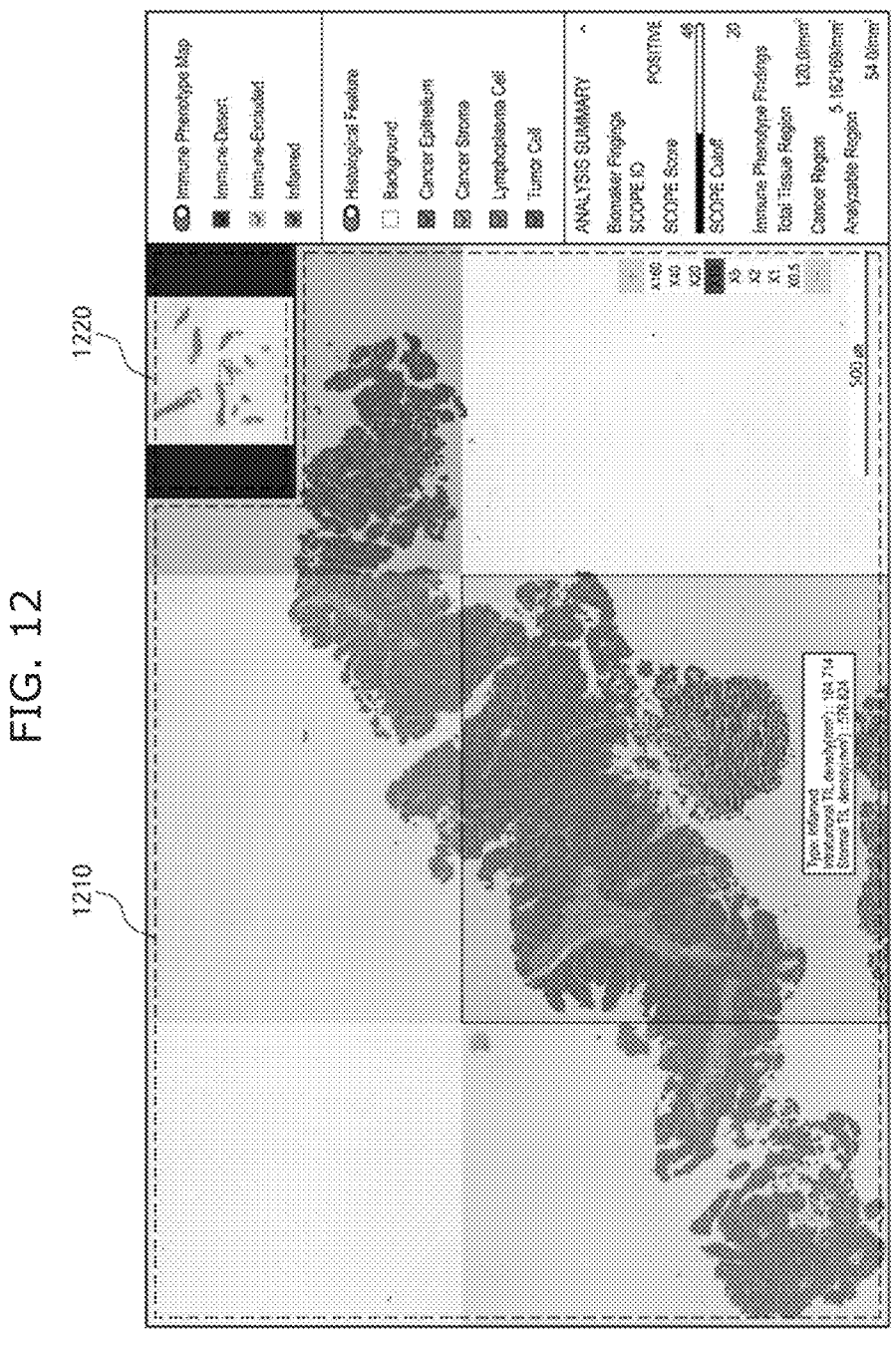
FIG. 12 is a diagram illustrating an example of outputting a detection result for target item and an immune phenotype determination result according to an embodiment.

FIG. 12 is a diagram illustrating an example of outputting a detection result for target item and an immune phenotype determination result according to an embodiment of the present disclosure. The processor (e.g., at least one processor of the user terminal) may output an image indicative of information (e.g., an immune phenotype map) associated with immune phenotype for one or more ROIs, Additionally, the processor may output an image indicative of the detection result for one or more target items. In an embodiment, the processor may overlay (or merge) an image indicative of the information associated with immune phenotype for one or more ROIs and/or the detection result for one or more target items on a corresponding region of the pathology slide image and output the result.

For example, as illustrated, the processor may display on the user interface an image 1210 displaying a first color indicative of immune desert, a second color indicative of immune excluded, a third color indicative of immune inflamed, a fourth color indicative of cancer epithelium region, a fifth color indicative of a cancer stromal region, a sixth color indicative of an immune cell (e.g., a center point of immune cell), and a seventh color indicative of a cancer cell (e.g., a center point of a cancer cell) are displayed on the corresponding region in the pathology slide images. In this example, the image 1210 may correspond to an image in which an image (e.g., an immune phenotype map) indicative of the information associated with immune phenotype for one or more ROIs and an image indicative of the detection result for one or more target items are overlaid on (or merged with) the corresponding region in the pathology slide image. Further, the first color, the second color, the third color, the fourth color, the fifth color, the sixth color and/or the seventh color may correspond to different colors that can be distinguished from each other.

Additionally or alternatively, the processor may also display on the user interface an image 1220 of at least some regions of the pathology slide image (e.g., regions corresponding to the image including the visual representation and/or the entire pathology slide image) separately (e.g., in a form of a minimap). Additionally or alternatively, as the information associated with immune phenotype, the processor may display on the user interface the visual representations corresponding to the respective target items (e.g., information on color corresponding to respective target items, and the like), text, numerical values, graphs, and the like for "analysis summary". Additionally or alternatively, a user interface may be output, through which the user may select the information associated with target item and/or immune phenotype to mark with a visual representation, in a corresponding region in the pathology slide image. In FIG. 12, color is used as an example of the visual representation to indicate the information associated with immune phenotype and/or target item, but embodiments are not limited thereto.

The above description of the present disclosure is provided to enable those skilled in the art to make or use the present disclosure. Various modifications of the present disclosure will be readily apparent to those skilled in the art, and the general principles defined herein may be applied to various modifications without departing from the spirit or scope of the present disclosure. Thus, the present disclosure is not intended to be limited to the examples described herein but is intended to be accorded the broadest scope consistent with the principles and novel features disclosed herein.

Although example implementations may refer to utilizing aspects of the presently disclosed subject matter in the context of one or more standalone computer systems, the subject matter is not so limited, and they may be implemented in conjunction with any computing environment, such as a network or distributed computing environment. Furthermore, aspects of the presently disclosed subject matter may be implemented in or across a plurality of processing chips or devices, and storage may be similarly influenced across a plurality of devices. Such devices may include PCs, network servers, and handheld devices.

Although the present disclosure has been described in connection with some embodiments herein, it should be understood that various modifications and changes can be made without departing from the scope of the present disclosure, which can be understood by those skilled in the art to which the present disclosure pertains. In addition, such modifications and changes should be considered within the scope of the claims appended herein.

What is claimed is:

1. A computing device comprising:
a memory storing one or more instructions; and
a processor configured to execute the stored one or more
instructions for:
   acquiring a digital image corresponding to an H&E-
     stained pathology slide;
   detecting, using a deep learning model executed by the
     processor, one or more target items including
     immune cells, a cancer area, and a cancer stroma
     area within a plurality of patches, wherein the plu-
     rality of patches are generated by dividing the digital
     image into equal-sized patches, and the deep learn-
     ing model is trained based on a reference pathology
     slide image and label information for one or more
     reference target items;
   determining, based on a density of immune cells in the
     cancer area and a density of immune cells in the
     cancer stroma area for each patch of the plurality of
     patches, immune phenotypes of first patches from
     among the plurality of patches that satisfy a prede-
     termined condition associated with at least one of a
     number of the immune cells, an area of the cancer
     area, or an area of the cancer stroma area, and
     excluding one or more second patches from among
     the plurality of patches that do not satisfy the pre-
     determined condition;
   generating a prediction result indicating whether a
     patient associated with the digital image responds to
     an immune checkpoint inhibitor, based on immune
     phenotype scores calculated from information asso-
     ciated with the immune phenotypes of the first
     patches from among the plurality of patches;
   overlaying a distinct visual representation for each of
     the first patches from among the plurality of patches
     on the digital image, the distinct visual representa-
     tion being indicative of the immune phenotype of the
     corresponding patch and comprising at least one of
     color, brightness, saturation, or a mark correspond-
     ing to the immune phenotype; and
   outputting, to a user, the digital image with the overlaid
     information and the prediction result, using a display
     device of the computing device.

2. A computing device according to claim 1, wherein the
overlaying and outputting includes:
   generating one or more visual representations correspond-
     ing to the immune phenotypes for the first patches; and
   overlaying and outputting the generated one or more
     visual representations on the digital image,
   wherein the immune phenotypes are determined based on
     at least one of a plurality of classes, each of which is
     indicative of an immune environment of a patch of the
     first patches, and
   wherein the image including the one or more visual
     representations includes:
     a first visual representation corresponding to a first
      class among the plurality of classes in a region
      corresponding to a patch of the first patches having
      an immune phenotype of the first class, and
     a second visual representation corresponding to a sec-
      ond class among the plurality of classes in a region
      corresponding to a patch of the first patches having
      an immune phenotype of the second class.

3. A computing device according to claim 1, wherein one
or more regions of interest (ROIs) are determined from
among the plurality of patches obtained by dividing the
digital image into equal sizes.

4. A computing device according to claim 1, wherein each
of the immune phenotypes is indicative of an immune
environment of the patch.

5. A computing device according to claim 1, wherein the
determining of the immune phenotypes comprises:
   determining an immune phenotype of a patch of the first
     patches as the immune inflamed, based on a first
     density of immune cells in the cancer area in the patch
     being greater than or equal to a first threshold density;
   determining the immune phenotype of the patch as the
     immune excluded, based on the first density of immune
     cells in the cancer area in the patch being less than the
     first threshold density and a second density of immune
     cells in the cancer stroma area in the patch being greater
     than or equal to a second threshold density; and
   determining the immune phenotype of the patch as the
     immune desert, based on the first density of immune
     cells in the cancer area in the patch being less than the
     first threshold density and the second density of
     immune cells in the cancer stroma area in the patch
     being less than the second threshold density.

6. A method, performed by at least one computing device,
for providing information associated with an immune phe-
notype for a digital image, comprising:
   acquiring a digital image corresponding to an H&E-
     stained pathology slide;
   detecting, using a deep learning model executed by the at
     least one computing device, one or more target items
     including immune cells, a cancer area, and a cancer
     stroma area within a plurality of patches, wherein the
     plurality of patches are generated by dividing the
     digital image into equal-sized patches, and the deep
     learning model trained, is trained based on a reference
     pathology slide image and label information for one or
     more reference target items, to detect one or more target
     items;
   determining, based on a density of immune cells in the
     cancer area and a density of immune cells in the cancer
     stroma area for each patch of the plurality of patches,
     the immune phenotypes of first patches from among the
     plurality of patches that satisfy a predetermined con-
     dition associated with at least one of a number of the
     immune cells, an area of the cancer area, or an area of
     the cancer stroma area, and excluding one or more
     second patches from among the plurality of patches that
     do not satisfy the predetermined condition;
   generating a prediction result indicating whether a patient
     associated with the digital image responds to an
     immune checkpoint inhibitor, based on immune phe-
     notype scores calculated from information associated
     with the immune phenotypes of the first patches from
     among the plurality of patches;
   overlaying a distinct visual representation for each of the
     first patches from among the plurality of patches on the
     digital image, the distinct visual representation being
     indicative of the immune phenotype of the correspond-
     ing patch and comprising at least one of color, bright-
     ness, saturation, or a mark corresponding to the
     immune phenotype; and
   outputting, to a user, the digital image with the overlaid
     information and the prediction result.

7. The method according to claim 6, wherein one or more
regions of interest (ROIs) are determined based on at least
one of the detection result for the cancer area in the patch or
the detection result for the cancer stroma area in the patch.

8. The method according to claim 6, wherein one or more
regions of interest (ROIs) are regions that satisfy the predetermined condition associated with the immune cells, the cancer area and the cancer stroma area.

9. The method according to claim 6, wherein one or more regions of interest (ROIs) are determined from among the plurality of patches obtained by dividing the digital image into equal sizes.

10. The method according to claim 6, wherein each of the immune phenotypes is indicative of an immune environment of the patch.

11. The method according to claim 6, further comprising:
calculating an inflamed score based on information associated with the immune phenotype for each of the first patches; and
outputting the prediction result indicating whether the patient, from which the digital image has been generated, responds to the immune checkpoint inhibitor, based on the inflamed score.

12. The method according to claim 6, wherein the determining includes:
calculating a density of the immune cells, for each of the first patches; and
determining the immune phenotype of each of the first patches based on the calculated density of the immune cells.

13. The method according to claim 12, wherein the calculating includes calculating, for each of the first patches, a density of the immune cells in the cancer area in the patch and a density of the immune cells in the cancer stroma area in the patch.

14. The method according to claim 6, further comprising:
outputting at least one of an area of total tissue area in the digital image, an area of total cancer area in the digital image, an area of total regions of interest (ROIs), a graph showing proportions of immune phenotypes, an inflamed score calculated based on information associated with the immune phenotype for each of the first patches, or cutoff information used to predict whether the patient, from which the digital image has been generated, responds to the immune checkpoint inhibitor.

15. The method according to claim 6, wherein:
the detecting includes detecting tumor cells, the immune cells, the cancer area, and the cancer stroma area in the digital image,
the method further comprises overlaying and outputting a detection result on the digital image, wherein the detection result includes a detection result for at least one of the tumor cells, the immune cells, the cancer area or the cancer stroma area.

16. The method according to claim 15, wherein the tumor cells, the immune cells, the cancer area, and the cancer stroma area are visually different from each other on the digital image.

17. A non-transitory computer-readable recording medium storing a computer program for executing, on a computer, the method for providing the information associated with the immune phenotype for the digital image according to claim 6.

18. The method according to claim 6, wherein the determining of the immune phenotypes comprises:
determining an immune phenotype of a patch of the first patches as the immune inflamed, based on a first density of immune cells in the cancer area in the patch being greater than or equal to a first threshold density;
determining the immune phenotype of the patch as the immune excluded, based on the first density of immune cells in the cancer area in the patch being less than the first threshold density and a second density of immune cells in the cancer stroma area in the patch being greater than or equal to a second threshold density; and
determining the immune phenotype of the patch as the immune desert, based on the first density of immune cells in the cancer area in the patch being less than the first threshold density and the second density of immune cells in the cancer stroma area in the patch being less than the second threshold density.

19. The method according to claim 18, wherein the immune phenotype is determined based on at least one of a plurality of classes, each of which is indicative of an immune environment of the patch,
the image including the one or more visual representations includes:
a first visual representation corresponding to a first class among the plurality of classes in a region corresponding to a patch of the first patches having an immune phenotype of the first class, and
a second visual representation corresponding to a second class among the plurality of classes in a region corresponding to a patch of the first patches having an immune phenotype of the second class.

20. The method according to claim 19, wherein the first visual representation and the second visual representation are visually different from each other.

* * * * *